US009808372B2

(12) United States Patent
Inoue et al.

(10) Patent No.: US 9,808,372 B2
(45) Date of Patent: Nov. 7, 2017

(54) THERAPEUTIC INSTRUMENT AND ATTACHMENT THEREOF

(75) Inventors: Masanobu Inoue, Honjo (JP); Kikuo Mitomo, Honjo (JP); Masako Oooka, Tokyo (JP); Kazuyuki Tokumo, Singapore (SG)

(73) Assignee: Hoya Corporation, Tokyo (JP)

( * ) Notice: Subject to any disclaimer, the term of this patent is extended or adjusted under 35 U.S.C. 154(b) by 558 days.

(21) Appl. No.: 13/813,950

(22) PCT Filed: Aug. 2, 2011

(86) PCT No.: PCT/JP2011/067665
§ 371 (c)(1),
(2), (4) Date: May 25, 2013

(87) PCT Pub. No.: WO2012/018006
PCT Pub. Date: Feb. 9, 2012

(65) Prior Publication Data
US 2013/0245554 A1    Sep. 19, 2013

(30) Foreign Application Priority Data

Aug. 3, 2010 (JP) .................. 2010-174336
Feb. 16, 2011 (JP) .................. 2011-030323

(51) Int. Cl.
| A61F 9/00 | (2006.01) |
| A61M 37/00 | (2006.01) |
| A61F 2/14 | (2006.01) |

(52) U.S. Cl.
CPC ............ *A61F 9/0017* (2013.01); *A61F 2/148* (2013.01); *A61M 37/0069* (2013.01)

(58) Field of Classification Search
CPC .......... A61M 37/0069; A61M 25/0084; A61M 5/3286; A61F 9/0017; A61F 2/1678;
(Continued)

(56) References Cited

U.S. PATENT DOCUMENTS 4,588,395 A * 5/1986 Lemelson .......... A61B 5/02154
600/7
4,836,201 A * 6/1989 Patton ................... A61F 2/1678
606/107
(Continued)

FOREIGN PATENT DOCUMENTS

JP    2004-024852    1/2004
JP    2008-173333    7/2008
(Continued)

OTHER PUBLICATIONS

International Search Report dated Oct. 25, 2011 for PCT App. Ser. No. PCT/JP2011/067665.
(Continued)

*Primary Examiner* — Kevin C Sirmons
*Assistant Examiner* — William Carpenter
(74) *Attorney, Agent, or Firm* — Henricks, Slavin & Holmes LLP

(57) ABSTRACT

There is provided a therapeutic instrument, for storing a sheet-type therapeutic substance to which a liquid is delivered, and delivering the stored therapeutic substance to an affected part, including: a nozzle member 23 having an opening 34 on a tip end of a tubular part 31 in which the therapeutic substance can be stored, for charging and discharging the therapeutic substance; and a syringe unit 22 that selectively causes a negative pressure and a positive pressure to act in the tubular part 31 through a hole of a valve member 27, wherein the space 33 of the tubular part 31 is the space for sucking the therapeutic substance into the tubular part 31 together with the liquid by causing the negative pressure in the tubular part 31 by the syringe unit 22 when the therapeutic substance is stored therein, and is the space for pushing out the therapeutic substance to outside of the tubular part 31 together with the liquid by causing the positive pressure to act in the tubular part 31 by the syringe (Continued)

unit 22 when the stored therapeutic substance is delivered to the affected part.

14 Claims, 21 Drawing Sheets

(58) Field of Classification Search
CPC .......... A61F 2/142; A61F 2/148; A61F 9/007; A61B 17/3468
See application file for complete search history.

(56) References Cited

U.S. PATENT DOCUMENTS

| | | | | |
|---|---|---|---|---|
| 4,880,000 | A * | 11/1989 | Holmes | A61F 2/1678 606/107 |
| 6,554,803 | B1 * | 4/2003 | Ashman | A61M 37/00 433/89 |
| 7,048,710 | B1 * | 5/2006 | Cragg | A61B 17/0057 604/15 |
| 8,382,769 | B2 * | 2/2013 | Inoue | A61F 2/167 606/107 |
| 8,460,311 | B2 * | 6/2013 | Ishii | A61F 2/1678 606/107 |
| 8,470,032 | B2 * | 6/2013 | Inoue | A61F 2/1678 606/107 |
| 2007/0208422 | A1 * | 9/2007 | Walter | A61F 2/142 623/5.11 |
| 2008/0281341 | A1 | 11/2008 | Miller et al. | |
| 2008/0294093 | A1 * | 11/2008 | Maeda | A61B 17/3468 604/60 |
| 2014/0012278 | A1 | 1/2014 | Mita | |

FOREIGN PATENT DOCUMENTS

| | | |
|---|---|---|
| JP | 2008173333 A * | 7/2008 |
| JP | 2009-000511 | 1/2009 |
| JP | 2009-524486 | 7/2009 |
| WO | WO 2007/089508 A2 | 8/2007 |

OTHER PUBLICATIONS

Extended European Search Report dated Apr. 7, 2017 for corresponding EPO App. Ser. No. 11814631.5.

* cited by examiner

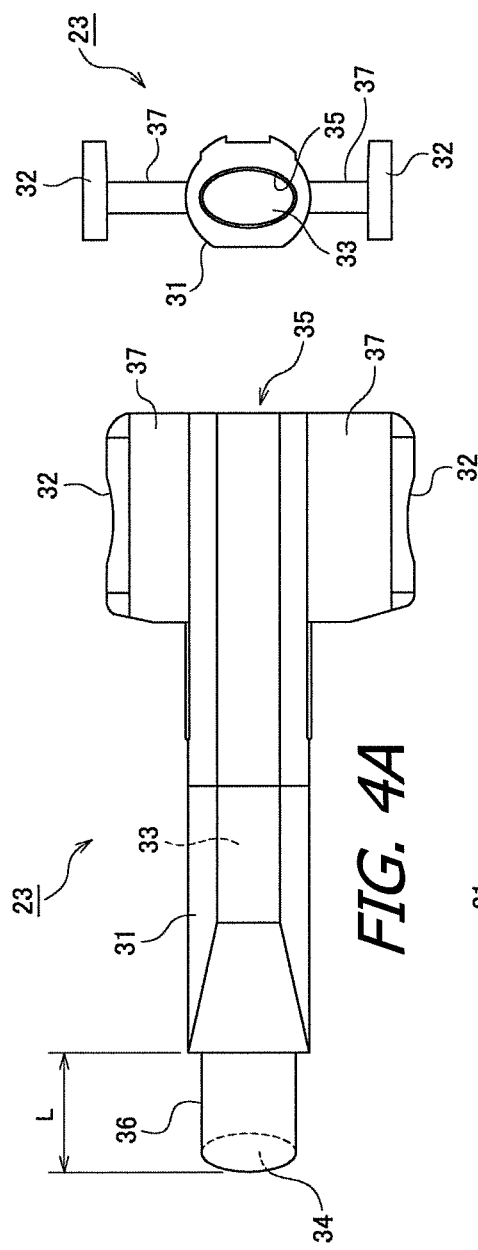
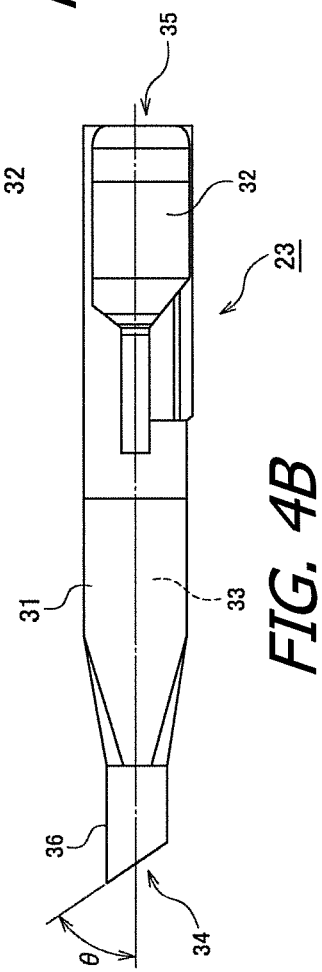
FIG. 4A  FIG. 4B  FIG. 4C

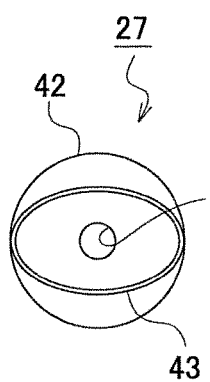
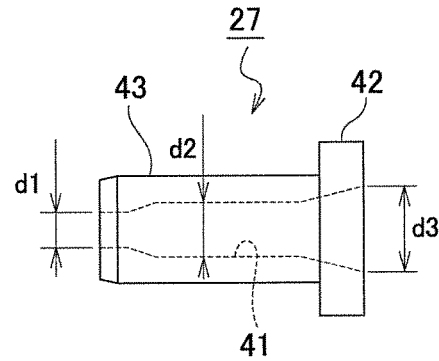
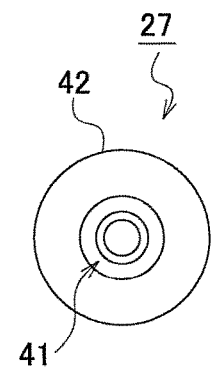
FIG. 5A  FIG. 5B  FIG. 5C
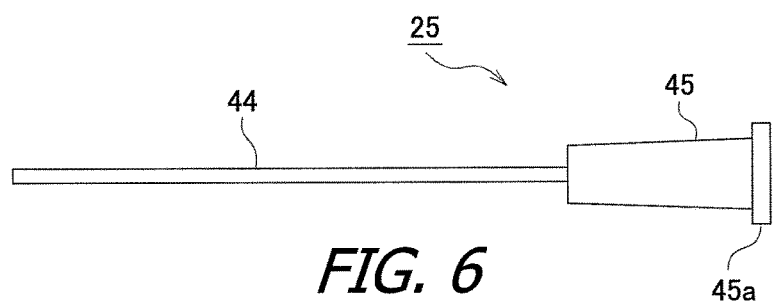
FIG. 6

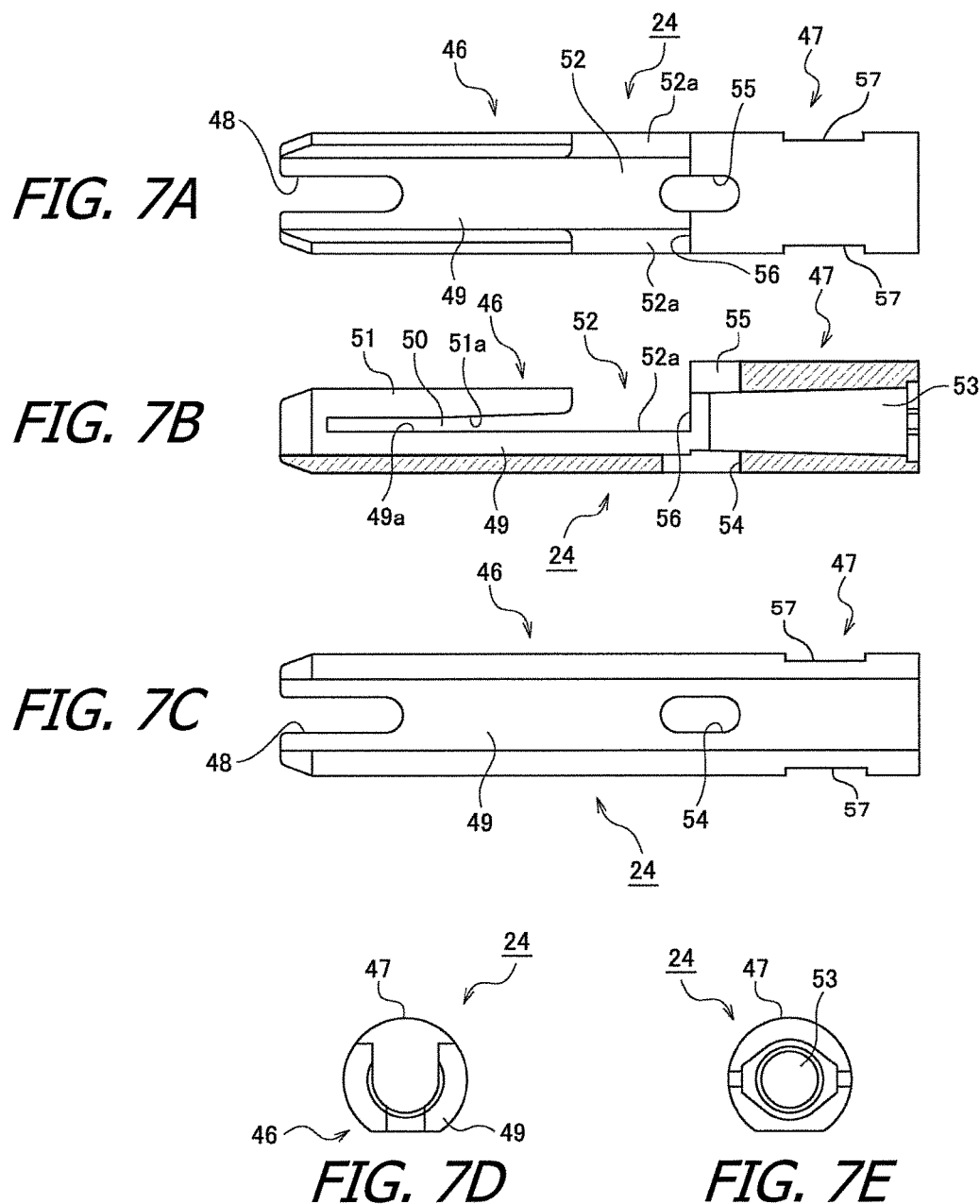

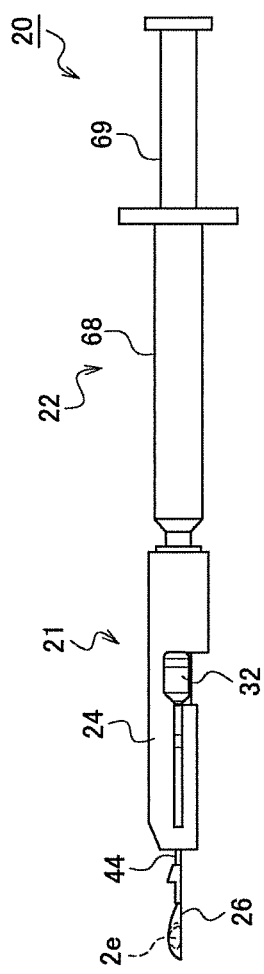
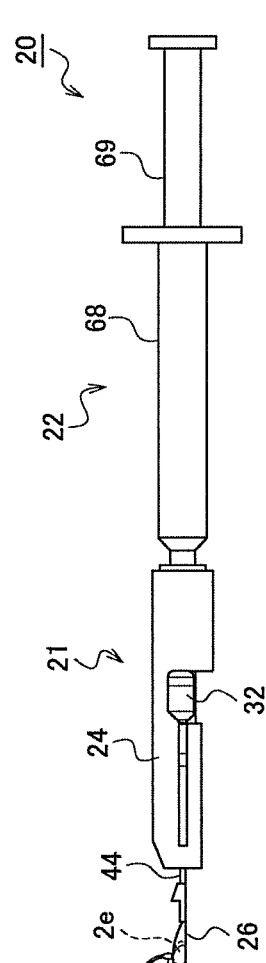
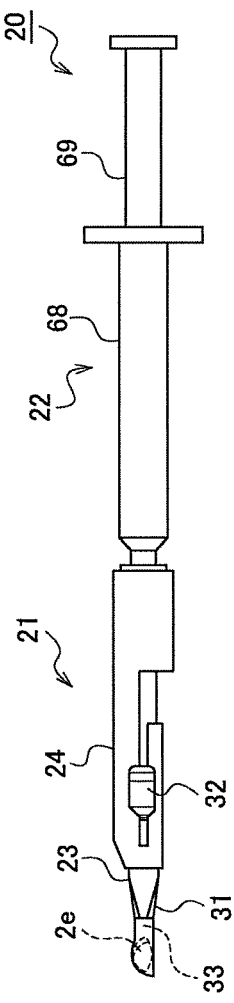
FIG. 12A
FIG. 12B
FIG. 12C

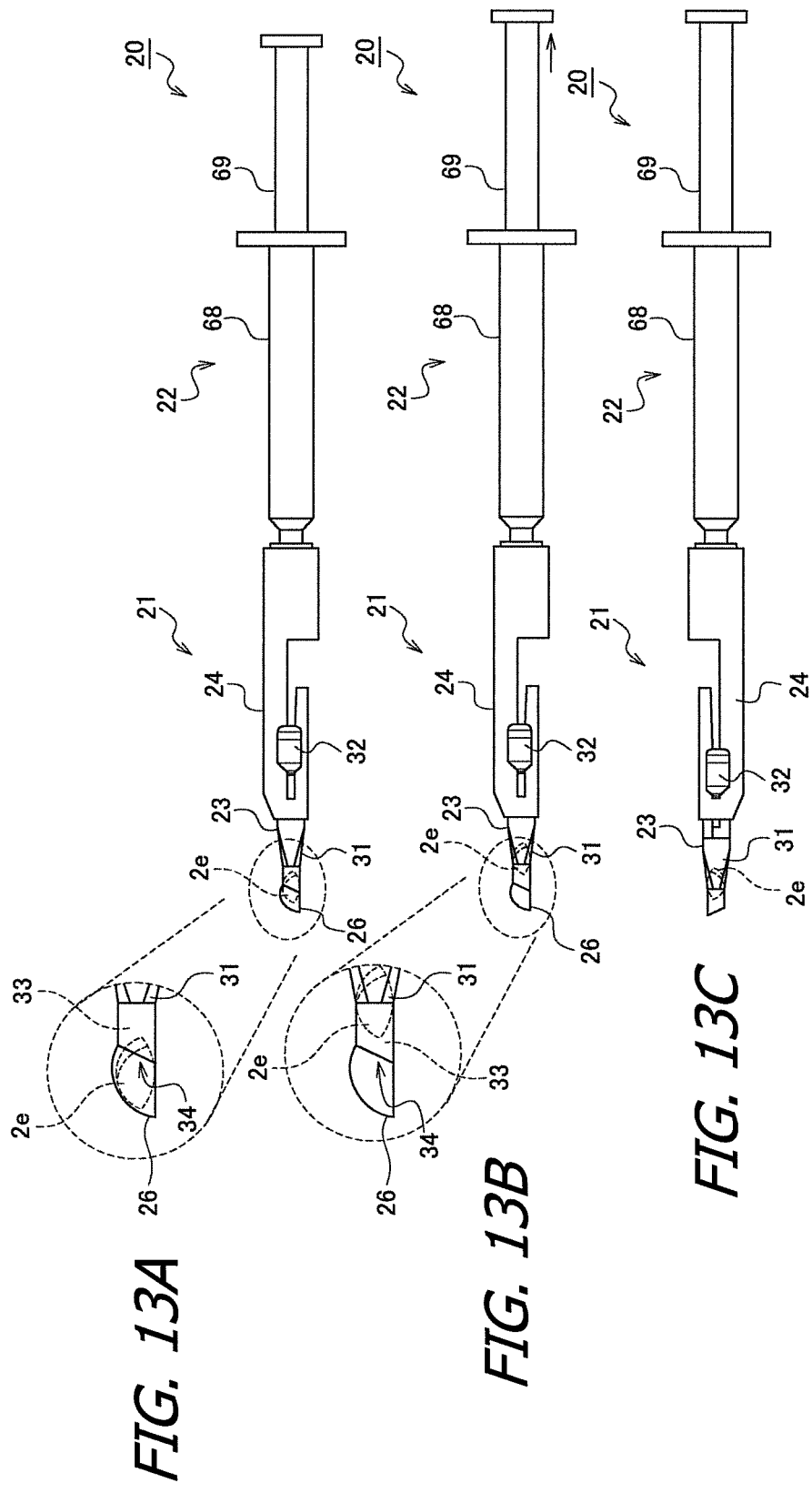

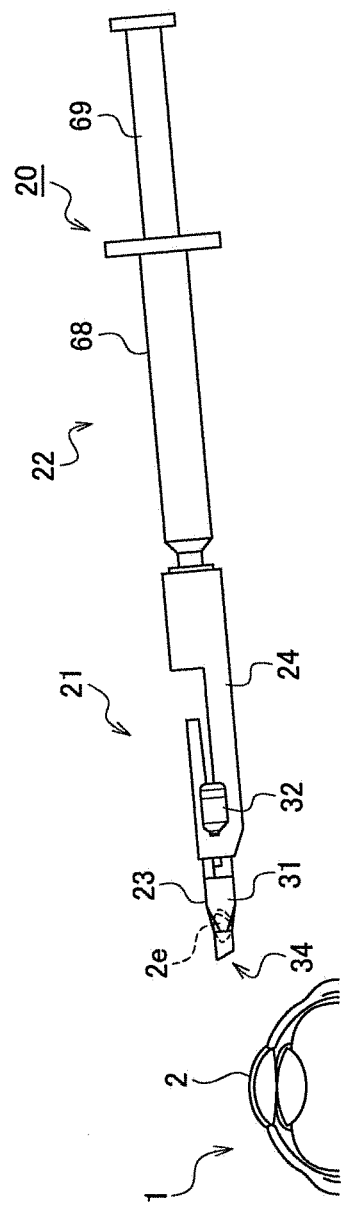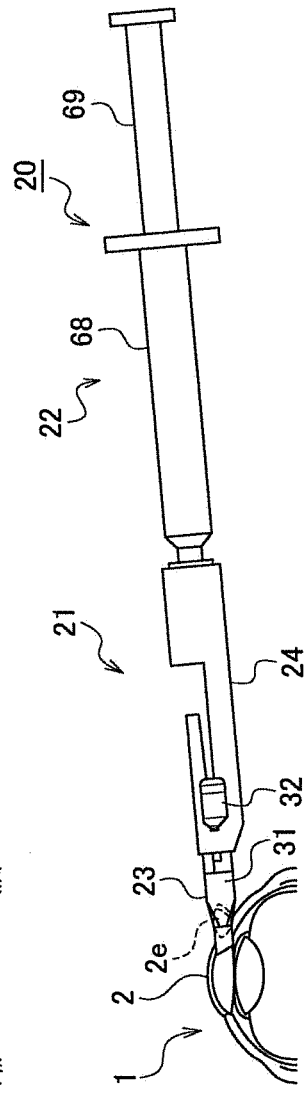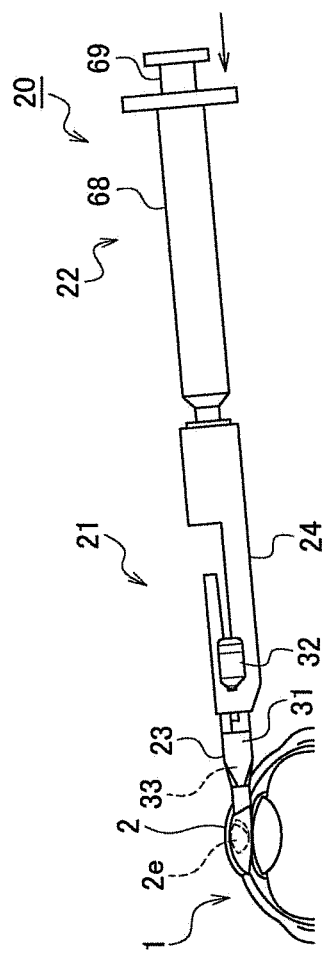
FIG. 14A
FIG. 14B
FIG. 14C

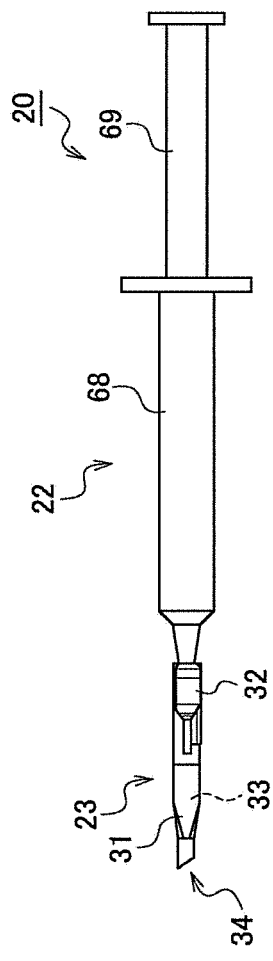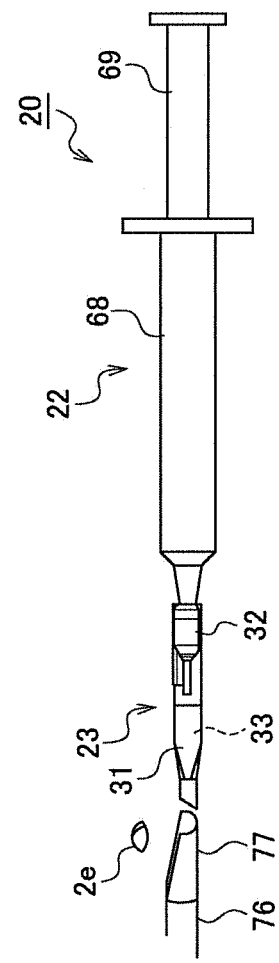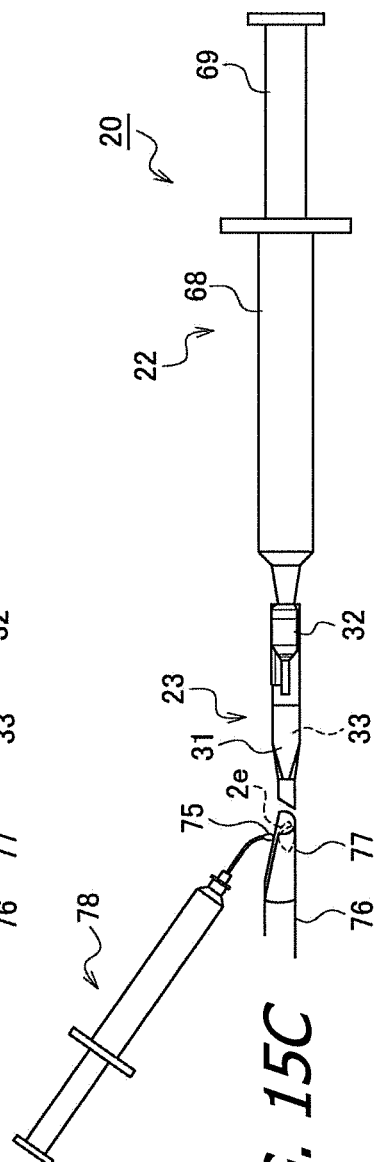
FIG. 15A
FIG. 15B
FIG. 15C

THERAPEUTIC INSTRUMENT AND ATTACHMENT THEREOF

CROSS REFERENCE TO RELATED APPLICATIONS

This application is a National Stage Entry of PCT/JP2011/067665, filed 2 Aug. 2011, and published as WO 2012/018006 on 9 Feb. 2012, which claims priority to JP2010-174336, filed 3 Aug. 2010, and JP2011-030323, filed 16 Feb. 2011.

TECHNICAL FIELD

The present invention relates to a therapeutic instrument and an attachment thereof used for delivering a sheet-type therapeutic substance to an affected part.

DESCRIPTION OF RELATED ART

There are proposed a plurality of treatment techniques of culturing and reconstructing a cell collected from a patient or a donor into a sheet type, and transplanting such a cell-sheet into an affected part (for example, see patent document 1). An application range of the treatment technique using the cell-sheet extends to a wide range. For example, this kind of treatment technique is applied not only to a treatment of a corneal endothelium disorder and a treatment of a deficient tissue of a retina in an ophthalmologic field, but also to a treatment of a myocardial infarction, and a treatment of an endoscopic resected place of a gastrointestinal inner wall, and so forth. This kind of treatment requires the following points: a degree of an invasion to a human body is low when delivering the cell-sheet to the affected part; a fragile cell-sheet can be protected; the cell-sheet can be developed into a proper shape when being transplanted into the affected part without being damaged; and handling in transplant is excellent.

As a therapeutic instrument for delivering the sheet-type therapeutic substance such as the above-mentioned cell-sheet to the affected part, an applicant of the present invention proposes an instrument including a cylindrical outer tube; a slide member slidably supported in the outer tube; and a sheet-type supporting member supporting the sheet-type therapeutic substance and provided on a tip end of the slide member, and maintained in a planar developed state in a free state of protruding from the tip end of the outer tube, and housed in the outer tube while deforming into a roll-shape when it abuts on the tip end of the outer tube at the time of moving in an internal direction of the outer tube, which is associated in conjunction with a sliding movement of the slide member (more specifically, see patent document 2).

Further, in the related art, a medical tool specialized for Deep Lamellar Endothelial Keratoplasty (DLEK) is also proposed (see patent document 3). In this medical tool, a cornea donor disk is supported by a soft substrate protruded from a tool body, and the soft substrate is taken in and out of the tool body by a mechanical driving mechanism using a plunger, etc.

PRIOR ART DOCUMENT

Patent Document

Patent document 1:
Japanese Patent Laid Open Publication No. 2004-24852

Patent document 2:
Japanese Patent Laid Open Publication No. 2009-511
Patent document 3:
Japanese Patent Laid Open Publication No. 2009-524486

SUMMARY OF THE INVENTION

Problem to be Solved by the Invention

The therapeutic instrument described in the above-mentioned patent document 2 is obtained at a relatively low cost, and has an advantage that handling is easy. However, the sheet-type supporting member is developed together with the treatment substance during transplant into a cornea portion. Therefore, the therapeutic instrument of patent document 2 is slightly not suitable for the transplant into a narrow space.

Meanwhile, the medical tool described in the above-mentioned patent document 3 involves the following problem. Namely, when the soft substrate supporting the cornea donor disk is drawn by the driving mechanism to thereby store it into the tool body, the cornea donor disk is caught by the tool body, and a storing state of the cornea donor disk becomes incomplete easily. As a result, when the cornea donor disk is pushed-out from the tool body, the cornea donor disk is clogged in the tool body in some cases, thus being lack in reliability.

A main object of the present invention is to provide a therapeutic instrument capable of increasing a reliability in push-out of a therapeutic substance, when the sheet-type therapeutic substance is stored in a cylindrical space, and thereafter delivering the therapeutic substance to an affected part.

Means for Solving the Problem

According to a first aspect of the present invention, there is provided a therapeutic instrument, for storing a sheet-type therapeutic substance therein, and delivering the stored therapeutic substance to an affected part, including:

a nozzle member having a tubular part forming a space in which the therapeutic substance can be stored in a deformed state, and having an opening on a tip end of the tubular part for charging and discharging the therapeutic substance, and having a communication part on a rear end of the tubular part for communicating with the space of the tubular part; and a pressure generator that selectively causes a negative pressure and a positive pressure to act in the tubular part of the nozzle member, wherein the space of the tubular part is the space for causing the negative pressure to act in the tubular part by the pressure generator to thereby suck the therapeutic substance into the tubular part, when the therapeutic substance is stored in the tubular part, and is the space for causing the positive pressure to act in the tubular part by the pressure generator to thereby push-out the therapeutic substance to outside of the tubular part, when the therapeutic substance stored in the tubular part by sucking is delivered to the affected part.

According to a second aspect of the present invention, there is provided the therapeutic instrument of the first aspect, further including:

a needle member having a hollow needle part inserted into the tubular part from a rear end side of the nozzle member, and capable of moving relatively to the nozzle member; and a supporting member fitted to a tip end of the needle member for supporting the therapeutic substance.

According to a third aspect of the present invention, there is provided the therapeutic instrument of the first or the second aspect, wherein a liquid is previously delivered to the sheet-type therapeutic substance, and the space of the tubular part is the space for sucking the therapeutic substance into the tubular part together with the liquid by an action of the negative pressure, when the therapeutic substance is stored in the tubular part, and is the space for pushing-out the therapeutic substance to outside of the tubular part together with the liquid by an action of the positive pressure, when the therapeutic substance stored in the tubular part by sucking is delivered to the affected part.

According to a fourth aspect of the present invention, there is provided the therapeutic instrument of the second or the third aspect, wherein the supporting member includes a tongue-like member having a planar developed shape in a state that the tip end of the needle part is protruded to outside of the tubular part, and having a shape deformed into a roll-shape in contact with an edge of the opening of the tubular part when the tip end of the needle part is retracted into the tubular part from the opening.

According to a fifth aspect of the present invention, there is provided the therapeutic instrument of the second, the third or the fourth aspect, wherein the communication part is a hole provided on the rear end of the tubular part, and the needle part is engaged with the hole.

According to a sixth aspect of the present invention, there is provided the therapeutic instrument of any one of the second to fifth aspects, wherein the needle member has a movable stopper which is engaged with the needle part and fixed thereto and moves through the tubular part together with the needle part while air-tightly sealing the space in the tubular part.

According to a seventh aspect of the present invention, there is provided the therapeutic instrument of any one of the second to sixth aspects, further including:
a holding member having a first holding part that holds the nozzle member in a state that the nozzle member and the needle member are allowed to move relatively to each other, and a second holding part that holds a base part of the needle member in a fixed state.

According to an eighth aspect of the present invention, there is provided the therapeutic instrument of the seventh aspect, wherein the holding member has a unit for regulating a movement terminal end position when the nozzle member and the needle member are relatively moved.

According to a ninth aspect of the present invention, there is provided the therapeutic instrument of any one of the second to eighth aspects, wherein the pressure generator includes a syringe unit having a syringe and a plunger.

According to a tenth aspect of the present invention, there is provided the therapeutic instrument of any one of the second to ninth aspects, including an attached unit for causing the negative pressure to act in the tubular part by a relative movement of the nozzle member and the needle member.

According to an eleventh aspect of the present invention, there is provided the therapeutic instrument of the tenth aspect, wherein the pressure generator has a movable part that selectively causes the negative pressure and the positive pressure to act in the tubular part of the nozzle member through the hole, and the attached unit includes a first moving unit that relatively moves the nozzle member and the needle member; a second moving unit that moves the movable part of the pressure generator; and a driving unit that concurrently moves the first moving unit and the second moving unit.

According to a twelfth aspect of the present invention, there is provided the therapeutic instrument of the eleventh aspect, wherein the driving unit moves the first moving unit and the second moving unit, so that the second moving unit starts to move the movable part of the pressure generator, after the first moving unit starts to move the nozzle member and the needle member relatively.

According to a thirteenth aspect of the present invention, there is provided the therapeutic instrument of the tenth aspect, wherein the attached unit is composed of the movable stopper engaged with the needle part and fixed thereto, and the movable stopper causes the negative pressure to be generated in the tubular part by integral movement of the nozzle member and the needle part in the tubular part while air-tightly sealing the space in the tubular part, when the nozzle member and the needle member are relatively moved so as to retract the supporting member into the tubular part.

According to a fourteenth aspect of the present invention, there is provided the therapeutic instrument of the thirteenth aspect, wherein the supporting member is formed integrally with the movable stopper.

According to a fifteenth aspect of the present invention, there is provided an attachment used for handling a therapeutic instrument that stores a sheet-type therapeutic substance therein for delivering the stored therapeutic substance to an affected part, the therapeutic instrument including:
a nozzle member having a tubular part forming a space in which the therapeutic substance can be stored in a deformed state, and having an opening on a tip end of the tubular part for charging and discharging the therapeutic substance, and having a communication part on a rear end for communicating with the space of the tubular part;
a pressure generator having a movable part for selectively causing a negative pressure and a positive pressure to act in the tubular part of the nozzle member;
a needle member having a hollow needle part inserted into the tubular part from a rear end side of the nozzle member and capable of moving relatively to the nozzle member; and
a supporting member fitted to a tip end of the needle member for supporting the therapeutic substance,
wherein the space of the tubular part is the space for causing the negative pressure to act in the tubular part by the pressure generator to thereby suck the therapeutic substance into the tubular part together with the liquid by an action of the negative pressure, when the therapeutic substance is stored in the tubular part, and is the space for causing a positive pressure to act in the tubular part by the pressure generator to thereby push-out the therapeutic substance to outside of the tubular part together with the liquid by an action of the positive pressure, when the therapeutic substance stored in the tubular part by sucking is delivered to the affected part, and the attachment including:
a first moving unit that relatively moves the nozzle member and the needle member;
a second moving unit that moves the movable part of the pressure generator; and a driving unit that concurrently moves the first moving unit and the second moving unit.

Effect of the Invention

According to the present invention, there is provided a therapeutic instrument capable of increasing reliability in push-out of a therapeutic substance, when a sheet-type therapeutic substance is stored in a cylindrical space and thereafter pushing and delivering the therapeutic substance to an affected part.

BRIEF DESCRIPTION OF THE DRAWINGS

FIGS. 4A-4C are top side and end views of a nozzle member.

FIGS. 4A-4C are end, side and end views of a valve member.

FIG. 6 is a side view showing a structure of a needle member.

FIGS. 7A-7E are top, side sectional, bottom, front and rear views of a holding member.

FIGS. 12A-12C are side views (second views) showing the use method of the therapeutic instrument according to the first embodiment of the present invention.

FIGS. 13A-13C are side views (third views) showing the use method of the therapeutic instrument according to the first embodiment of the present invention.

FIGS. 14A-14C are side views (fourth views) showing the use method of the therapeutic instrument according to the first embodiment of the present invention.

FIGS. 15A-15C are side views (first views) showing the structure and the use method of the therapeutic instrument according to a second embodiment of the present invention.

MODES FOR CARRYING OUT THE INVENTION

An embodiment in a case of applying a therapeutic instrument of the present invention to a surgical instrument used for an ophythalmic operation for example, more specifically in a case of applying the therapeutic instrument of the present invention to a therapeutic instrument used for Descemet's Stripping Automated Endothelial Keratoplasty (DSAEK) effective for a treatment of a corneal endothelial cell disorder, will be described hereafter, with reference to the drawings. The therapeutic instrument of the present invention is not limited to an application to an ophthalmic operation instrument, and can be applied to a surgical instrument for a medical treatment other than an ophthalmic treatment, and can be applied to a general purpose of use other than the medical treatment, such as an instrument for each kind of experiment (or test).

Explanation is given for an embodiment of the present invention in the following order.
1. Structure of an Eyeball
2. Structure of a Therapeutic Instrument of a First Embodiment
3. Method of Manufacturing the Therapeutic Instrument (assembly procedure)
4. Use Method of the Therapeutic Instrument
5. Effect of the First Embodiment
6. Second Embodiment
7. Effect of the Second Embodiment
8. Third Embodiment
9. Effect of the Third Embodiment
10. Fourth Embodiment
11. Effect of the Fourth Embodiment
12. Modified Example, etc.

1. Structure of Eyeball

The Whole Structure of Eyeball

Figure 1:
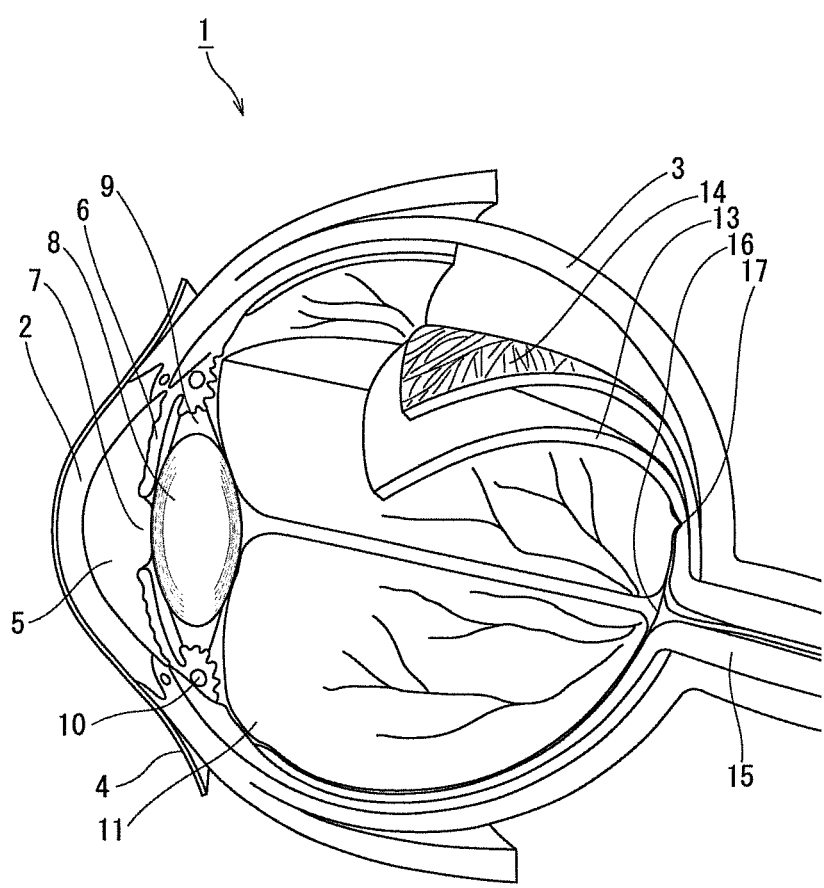
FIG. 1 is a view describing a planar cross-sectional structure of an eyeball.

FIG. 1 is a view describing a planar cross-sectional structure of an eyeball. As shown in the figure, an eyeball 1 is formed into a spherical shape, and coated and protected by a sclera 3 excluding a portion of an anterior cornea 2. A surface of the sclera 3 around the cornea 2 is covered with a conjunctiva 4. The cornea 2 has a lens function of refracting a light entered from outside, in addition to an eyeball protecting function. An anterior chamber 5 filled with aqueous humor exists inside (on the rear side) of the cornea 2, and a pupil 7 exists in the center of an iris 6 facing the anterior chamber 5.

The iris 6 has a function of adjusting a quantity of the light incident on an inside of the eyeball 1, by adjusting a size of the pupil 7 (dimension of an opening). A front face of a crystalline lens 8 is disposed in face of the pupil 7. A ciliary body 10 is connected to the crystalline lens 8 through a zonula ciliaris 9. The ciliary body 10 is a muscle tissue that performs focusing by controlling a thickness of the crystalline lens 8.

A vitreous body 11 exists on the rear side of the crystalline lens 8. The vitreous body 11 occupies a major part of the inside of the eyeball 1. The vitreous body 11 is a transparent and colorless jelly tissue, and maintains a shape and elasticity of the eyeball 1. Further, the vitreous body 11 has a function of sending a light beam refracted by the crystalline lens 8 to a retina 13. The retina 13 is a film tissue positioned innermost side in the eyeball 1. A photoreceptor cell for feeling the light incident into the eyeball 1 through the pupil 7, and identifying its intensity, color, and shape, exists in the retina 13.

A choroid 14 exists outside of the retina 13. The choroid 14 is a film tissue positioned inside of the sclera 3 (namely, between the sclera 3 and the retina 13). The choroid 14 is rich in blood vessels, and has a function of nourishing the eyeball 1, as a blood channel to each tissue of the eyeball 1. Further, an optic nerve 15 is connected to the backside (rear side) of the eyeball 1. The optic nerve 15 is a nerve that transmits a light stimulation received by the retina 13, to a brain. A blind spot 16 exists at a portion to which the optic nerve 15 is connected. The blind spot 16 is positioned at a distance of 4 to 5 mm from a fovea centralis 17.

Structure of the Cornea

Figure 2:
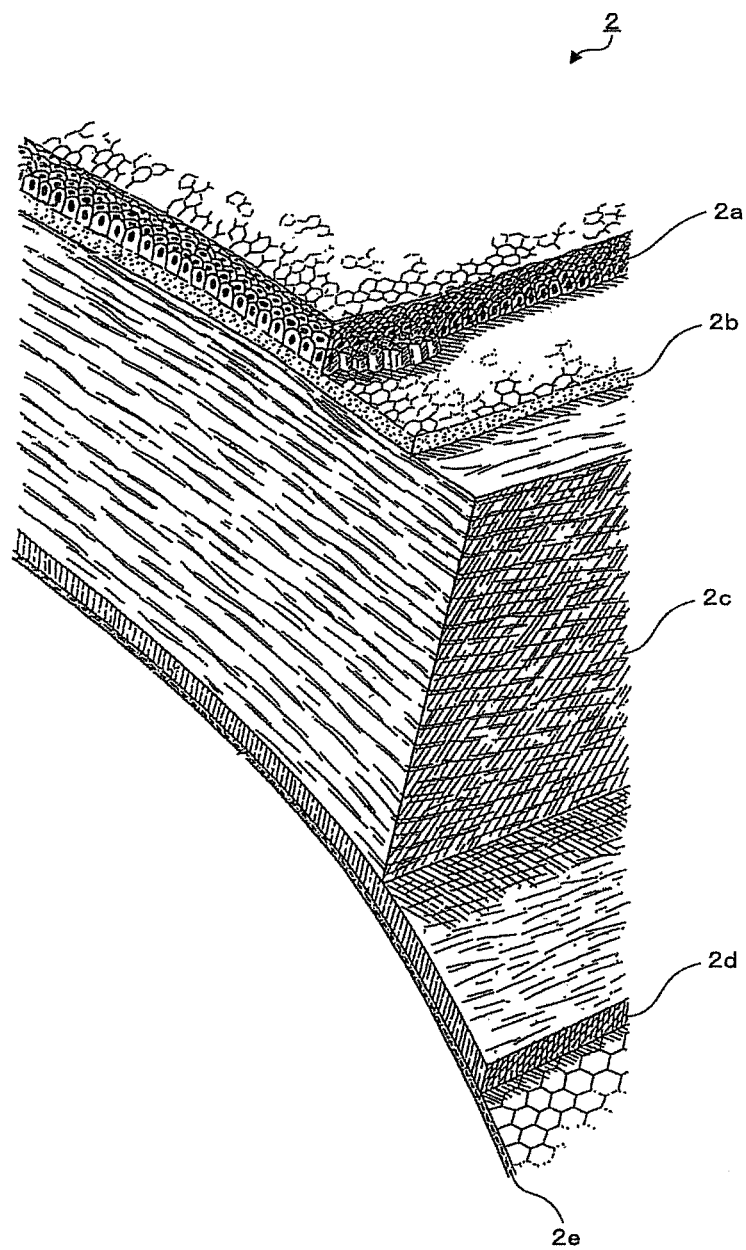
FIG. 2 is a schematic view three-dimensionally showing a structure of a cornea.

FIG. 2 is a schematic view three-dimensionally showing the structure of the cornea. The cornea 2 has a multilayer lamination structure. Specifically, the cornea 2 has a structure of laminating a corneal epithelial layer 2a, a Bowman's membrane 2b, a corneal stromal layer 2c, a Descemet membrane (posterior limiting lamina of cornea) 2d, and a corneal endothelium layer 2e.

The corneal epithelial layer 2a exists on an outermost layer of the cornea 2, and is formed of 5 to 6 layers of a multilayer squamous cell. The Bowman's membrane 2b exists between the corneal epithelial layer 2a and the corneal stromal layer 2c, and is composed of collagen fiber with a thickness of about 10 μm.

The corneal stromal layer 2c exists between the Bowman's membrane 2b and the Descemet membrane 2d, and occupies 90% of a corneal whole layer. The Descemet membrane 2d exists between the corneal stromal layer 2c and the corneal endothelium layer 2e, and is composed of a fine fiber with a thickness of 5 to 10 μm. The corneal endothelium layer 2e exists innermost side of the cornea 2, and is composed of flat hexagonal one layer cell (corneal endothelial cell) with a thickness of 5 μm.

2. Structure of the Therapeutic Instrument of the First Embodiment

Figure 3:
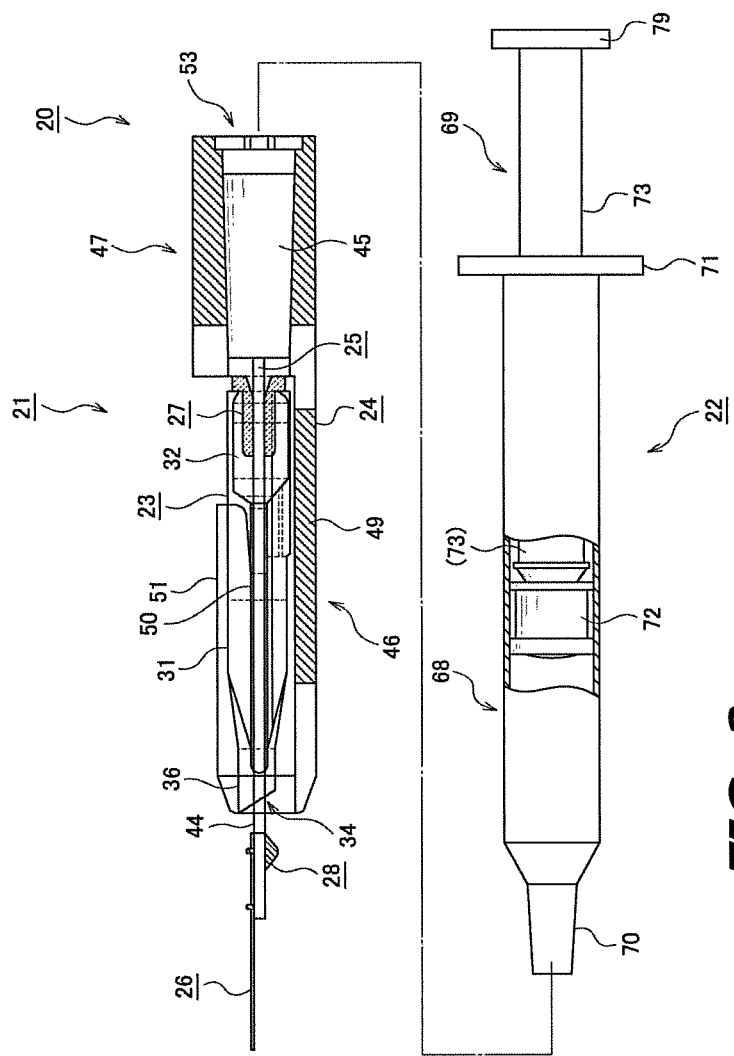
FIG. 3 is a cross-sectional view showing a structure of a therapeutic instrument according to a first embodiment of the present invention.

FIG. 3 is a cross-sectional view showing the structure of the therapeutic instrument according to the first embodiment of the present invention. A therapeutic instrument 20 shown in the figure stores therein a sheet-type therapeutic substance to which a liquid is delivered, and delivers the stored therapeutic substance to an affected part.

As described above, according to this embodiment, the therapeutic instrument is provided, which is used for a surgery of a corneal endothelium transplant effective for a treatment of the corneal endothelial cell disorder. Therefore, the therapeutic instrument of this embodiment is one of the instruments for surgery handled by an ophthalmologist who performs the corneal endothelium transplant surgery. Further, in such a transplant surgery, for example, the corneal endothelium layer collected from a donor and cultured, corresponds to the sheet-type therapeutic substance. The corneal endothelium layer used for the transplant is a circular sheet-type substance with a diameter of about 8.0 to 9.0 mm. Further, delivery of the corneal endothelium layer is performed to a cornea portion of an eyeball (specifically a transplant target part of the corneal endothelium layer) being a disorder portion.

The therapeutic instrument 20 is mainly constituted of a body unit 21 and a syringe unit 22. The body unit 21 and the syringe unit 22 can be attached and detached to/from each other.

Structure of the Body Unit

The body unit 21 is mainly constituted of a nozzle member 23 being a main member of the therapeutic instrument 20; a holding member 24 holding the nozzle member 23; a needle member 25 moving relatively to the nozzle member 23 and integrally with the holding member 24 (described as simply "relative movement" hereafter); and a supporting member 26 attached to a needle point of the needle member 25. More specifically, in addition to these members, the body unit 21 is constituted of a valve member 27 and a connection piece 28. Each member is specifically described hereafter in an order of the nozzle member 23→valve member 27→needle member 25→holding member 24→supporting member 26→connection piece 28.

Nozzle Member

FIG. 4 is a view describing the structure of the nozzle member, and FIG. 4A is a planar view, FIG. 4B is a side view, and FIG. 4C is a view viewed from a rear edge side.

The nozzle member 23 has a main function of storing and delivering the corneal endothelium layer being the therapeutic substance. The nozzle member 23 is formed by a hollow member obtained by integral molding of resin. When the nozzle member 23 is made of resin, for example polypropylene can be suitably used as its constitutional material. The nozzle member 23 integrally includes a tubular part 31 and a pair of finger rest parts 32. The tubular part 31 has a cylindrical space 33 inside. The space 33 is formed into an oval shape in cross-section. Further, the space 33 is formed in a state of linearly passing through the tubular part 31 from a tip end to a rear end in a center axis direction of the tubular part 31.

Wherein, the tip end of the tubular part 31 is an end portion disposed at a side close to an affected part, when the therapeutic substance is delivered to the affected part using the therapeutic instrument 20, and the rear end of the tubular part 31 is an end portion disposed at an opposite side thereto, namely at a side far from the affected part. Regarding this point, the same thing can be said for other members.

The above-mentioned space 33 has a uniform sectional shape (oval shape) from the tip end to the rear end in the axis direction of the tubular part 31, and is formed having a uniform opening dimension. Further, an opening 34 is formed on the tip end of the tubular part 31 so as to lead to the space 33, and an opening 35 is formed on the rear end of the tubular part 31 so as to lead to the space 33. Each one of the openings 34, 35 is formed into an oval opening shape similarly to the sectional shape of the space 33. An outer shape of the tip end side of the tubular part 31 is tapered (flattened) toward a short axis direction of the opening 34. Further, a tip end side portion of the tubular part 31 is formed thinner than the tapered portion, and such a thin portion is formed as a beak part 36. The beak part 36 is a portion disposed to face the affected part, when the therapeutic substance is delivered to the affected part. The tip end of the beak part 36 has an obliquely cut shape with respect to the center axis of the nozzle member 23, when the nozzle member 23 is viewed from a side direction. The opening 34 exists in this oblique portion. Mainly two points can be given as the reason for forming the tip end of the tubular part 31 (beak part 36) into an oblique cut shape. As point 1, the corneal endothelium layer 2e is easily inserted into a corneal portion being an example of the affected part. As point 2, the tubular part 31 is easily inserted into an incised wound.

The thickness of the beak part 36 is preferably set to 0.05 to 0.2 mm for example, and further preferably set to about 0.6 mm for example. Further, the length L of the beak part 36 is preferably set in a range of 1 to 7 mm for example, and further preferably set to about 5 mm. The above-mentioned opening 34 is formed on the tip end of the beak part 36 into an oblique cut end face. An inclination angle $\Theta$ of the cut end face of the opening 34 is preferably set to $\Theta=45$ to $60°$ with respect to the center axis of the tubular part 31, and more preferably set to about 55°, for example, in consideration of easiness of supplying the therapeutic substance during transplant of the corneal endothelium transplant.

A pair of finger rest parts 32 are formed to be positioned at the rear end side of the tubular part 31, and at both sides on outer periphery of the tubular part 31. Each finger rest part 32 structurally leads to the tubular part 31 through corresponding blade parts 37. Each blade part 37 is formed into a plate-shape in a state of protruding in a diameter direction of the tubular part 31 (long axis direction of the opening 35) from the outer peripheral part of the tubular part 31. Each blade part 37 is formed on an axial line of a long axis of the opening 35, into a plate shape parallel to the long axis.

Meanwhile, as shown in FIG. 4C, a pair of finger rest parts 32 are formed into T-shape as a whole in a combination with the corresponding blade parts 37. Each finger rest part 32 is formed into a plate-shape approximately parallel to a short axis of the opening 35. A recess-shaped depression in planer view is formed respectively on an outer face of each finger rest part 32, in consideration of a stability at the time of actually gripping the nozzle member 23 by pressing a finger pad against the finger rest part 32. Further, the outer face of each finger rest part 32 is formed into an irregular surface in such a manner that a plurality of thin grooves not shown are arranged at a specific pitch in the axis direction of the tubular part 31 for example, to thereby suppress a slip of a finger when using the therapeutic instrument 20.

Valve Member

FIG. 5 is a view describing the structure of a valve member, wherein FIG. 5A is a view viewed from one side of the axis direction, FIG. 5B is a front view, and FIG. 5C is a view viewed from the other side of the axis direction.

The valve member 27 is one of the constitutional elements of the nozzle member 23 by being assembled and fixed to the above-mentioned nozzle member 23. Therefore, the nozzle member 23 and the valve member 27 may have an integral structure made of a resin molding. Here, explanation is given for a case that the nozzle member 23 and the valve member 27 are formed as a separate body, as an example.

The length (dimension in the center axis direction) of the valve member 27 is set to be sufficiently shorter than the length of the nozzle member 23.

For example, when the length of the nozzle member 23 is about 30 mm, the length of the valve member 27 is set to about 5 to 7 mm.

The valve member 27 is a cylindrical member formed into a hollow structure as a whole. A circular through hole 41 in cross-section, is formed inside of the valve member 27. The through hole 41 corresponds to the "communication part" leading to the space of the tubular part 31. The through hole 41 is a "hole" formed as an embodiment of the above-mentioned communication part, and is formed in a state passing through the valve member 27 in the axis direction. A hole size (diameter) of the through hole 41 is gradually larger toward the rear end side from the tip end side in the center axis direction of the valve member 27. Namely, a hole size d1 at the tip end side of the valve member 27 (through hole 41) is smaller than a hole size d2 at a deeper side (inner side) thereof, and a hole size d3 at the rear end side of the through hole 41 is larger than the hole size d2 at a deeper side (inner side) thereof. Further, in an area where the hole size of the through hole 41 is varied from d1 to d2, and in an area where it is varied from d2 to d3, the hole size is continuously varied respectively. In these hole sizes, when the hole size d1 at the tip end side of the through hole 41 is set to a dimension corresponding to an outer diameter of a needle of the needle member 25, for example in a case that the outer diameter of the needle is set to 0.9 mm, the hole size d1 can be set to about 0.7 to 0.9 mm. Further, the hole size of the through hole 41 is fixed to d1 in an area from the tip end of the valve member 27 to a specific dimension (for example dimension of about 0.5 mm) in the center axis direction of the valve member 27.

Here, as an example, a hole structure is employed as follows: the hole size at the rear end side of the through hole 41 is expanded in an outwardly opened state so as to continuously varied from d2 to d3. However, the hole structure is not limited thereto, and the following structure may be employed. Namely, the rear end of the through hole 41 is opened, with the hole size fixed to d2. Further, a straight structure may also be employed, with the hole size of the through hole 41 fixed to d1.

A flange part 42 is formed on a rear end portion of the valve member 27 integrally with the valve member 27. The flange part 42 is formed in a state that the rear end portion of the valve member 27 is expanded in a diameter direction. An outer shape of the flange part 42 is a circular shape if the valve member 27 is viewed from the center axis direction. Meanwhile, other part of the valve member 27 excluding the flange part 42 (part closer to the tip end than the flange part 42) is a nose part 43. An external peripheral edge of the tip end of the nose part 43 is chamfered. When the valve member 27 is viewed from the center axis direction, the outer shape of the nose part 43 is an oval shape corresponding to an open shape of the opening 35 of the above-mentioned tubular part 31. An outer dimension of the nose part 43 in the long axis direction, is the same dimension as the diameter of the flange part 42. The outer dimension of the nose part 43 in the short axis direction is a smaller dimension than the diameter of the flange part 42. The outer dimension of the nose part 43 thus formed into the oval shape, is set corresponding to the opening dimension of the opening 35 of the above-mentioned tubular part 31.

Needle Member

FIG. 6 is a side view showing the structure of the needle member. As shown in the figure, the needle member 25 has a needle part 44 and a base part 45. The needle part 44 is a long tubular portion made of metal. The needle part 44 is formed as a straight part. The base part 45 is a cylindrical portion made of resin. The needle part 44 and the base part 45 are arranged on the same axis. Further, the needle part 44 and the base part 45 are integrally connected to each other in a mutually communicable state. The tip end of the needle part 44 is not obliquely cut like a publicly-known injection needle for medical use, but is cut into a flat shape so as to be vertical to the center axis direction. The base part 45 is formed into a circular cylindrical shape as a whole, with the rear end portion formed as substantially an oval flange part 45*a*. The outer diameter of the base part 45 excluding the flange part 45*a* is continuously smaller toward the tip end side from the rear end side of the base part 45. Further, the base part 45 has a hollow part (hole part) having a circular shape in cross-section. The needle part 44 is fixed to the tip end side of the base part 45 in a state that the rear end (hole) of the needle part 44 is disposed in face of the hollow part of the base part 45.

Holding Member

FIG. 7 is a view describing the structure of the holding member, wherein FIG. 7(A) is a planar view, FIG. 7(B) is a side sectional view, FIG. 7(C) is a lower surface view, FIG. 7(D) is a view viewed from the tip end side, and FIG. 7(E) is a view viewed from the rear end side.

The holding member 24 is configured to hold the above-mentioned needle member 25 in a fixed state, and hold the above-mentioned nozzle member 23 in a relatively movable state. The "relative movement" described in this specification indicates a movement of two structurally independent two members relatively in the center axis direction of the needle part 44 of the needle member 25. Further, the center axis direction of the needle part 44 is a direction corresponding to the center axis direction of the tubular part 31 of the nozzle member 23, and the center axis direction of the therapeutic instrument 20.

The holding member 24 is a member obtained by integral molding of the resin such as polypropylene. A bottom surface of the holding member 24 is a flat surface with a part of the cylindrical surface notched. The holding member 24 is divided into a first holding part 46 and a second holding part 47 in the center axis direction of the holding member 24.

The first holding part 46 is a part for movably holding the nozzle member 23 so as to allow the relative movement of the nozzle member 23 and the needle member 25. A U-shaped groove part 48 is formed on the tip end side of the first holding part 46. Also, a nozzle receiving part 49 is formed in the first holding part 46. The nozzle receiving part 49 is formed in a vessel shape as a whole. A slit 50 is formed on the nozzle receiving part 49 along the center axis direction of the holding member 24. The slit 50 is configured to generate a proper braking force when the nozzle member 23 and the needle member 25 are relatively moved, to thereby regulate a movement terminal end position at one side of the nozzle member 23.

The slit 50 is formed by a rod-like beam 51 extending toward the rear end side from the tip end portion of the holding member 24. More specifically, the slit 50 is formed by an inside face 51*a* of the beam 51 and a guiding face 49*a* of the nozzle receiving part 49 which is opposed to the inside face 51*a*. The tip end of the slit 50 is closed, and the rear end of the slit 50 is opened. The slit 50 is formed having a width (called "slit width" hereafter) corresponding to the thickness of the blade part 37 of the nozzle member 23. The slit width of the slit 50 is set to be gradually larger from the middle, toward the rear end side from the tip end portion of the holding member 24.

Further, in the nozzle receiving part 49, the rod-shaped beam 51 having the slit 50 formed therein as described above, has a proper flexibility by elasticity of a material itself constituting the holding member 24. The flexibility of the beam 51 described here, means a property of the beam part 51 capable of elastically deforming in a slit width direction in a configuration of a cantilever beam, with a base end portion of the beam part 51 as a fixing end, and the opposite side thereto as a free end.

The guiding face 49*a* of the nozzle receiving part 49 is formed into a straight shape along the center axis of the holding member 24. Meanwhile, although the tip end side of the inside face 51*a* of the beam part 51 is formed into a straight shape along the center axis of the holding member 24, the rear end side thereof is formed into a taper shape having an inclination of about 15° for example, with respect to the center axis. The slit width of the slit 50 is varied in accordance with the taper shape of the inside face 51*a* of the beam part 51. Further, the width of a straight portion of the slit 50 is set to be slightly smaller (for example, about 0.1 to 0.2 mm) than the thickness of the blade part 37 of the nozzle member 23.

A notch part 52 is formed in a portion extending from the rear end of the beam part 51 to the second holding part 47. The notch part 52 is a portion for receiving the blade part 37 of the nozzle member 23 when the nozzle member 23 is assembled into the holding member 24. Therefore, the notch part 52 is formed in a state that an upper side of the first holding part 46 is opened. The bottom surface 52*a* of the notch part 52 is disposed on the same plane as the guiding face 49*a* of the nozzle receiving part 49.

The second holding part 47 is a portion for holding the base part 45 of the needle member 25 in a fixed state. The second holding part 47 is formed into an approximately a cylindrical shape as a whole. A fixing hole 53 with the center axis of the holding member 24 as a center, is formed in the second holding part 47. The fixing hole 53 is a portion where the base part 45 of the needle member 25 is fixed in an engagement state. Therefore, the hole size of the fixing hole 53 is set corresponding to the outer dimension of the base part 45 of the needle member 25. Specifically, as described above, the outer diameter of the base part 45 of the needle member 25 is continuously smaller toward the tip end side from the rear end side, and therefore the hole size of the fixing hole 53 is also continuously varied accordingly in the center axis direction of the holding member 24. Further, the opening shape of the rear end side of the fixing hole 53 is approximately an oval shape corresponding to the outer shape of the flange part 45*a* of the base part 45. When the base part 45 is engaged with the fixing hole 53 through the needle part 44, for example the base part 45 is fixed to the fixing hole 53 by press-fitting. Further, the needle part 44 linearly extending from the base part 45, is disposed on the same axis as the center axis of the holding member 24.

A long hole 54 is formed on a boundary between the first holding member 46 and the second holding part 47, along the center axis direction of the holding member 24. A U-shaped groove 55 is formed on the second holding part 47 in a positional relation in which the groove 55 is overlapped on the long hole 54. As described above, when the base part 45 of the needle member 25 is engaged with the fixing hole 53 and fixed thereto, these long hole 54 and the groove 55 are formed at a position where the boundary between the needle part 44 and the base part 45 can be visually recognized from outside.

Further, an abutting face 56 is formed on the boundary between the first holding part 46 and the second holding part 47. The abutting face 56 is formed in a state of vertically standing up from the above-mentioned guiding face 49*a*. The abutting face 56 is configured to regulate the other movement terminal end position of the nozzle member 23 when the nozzle member 23 and the needle member 25 are relatively moved.

Supporting Member

Figure 8A:
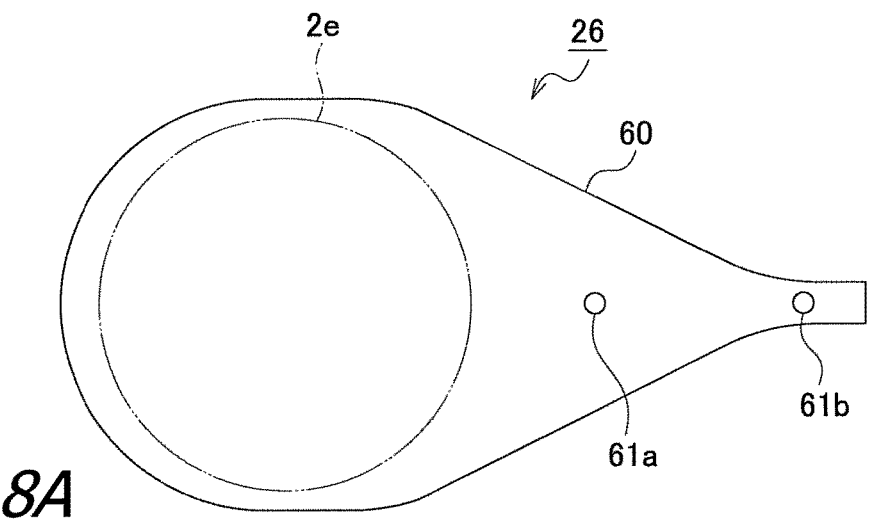
FIGS. 8A-8B are top and side views of a supporting member.
Figure 8B:
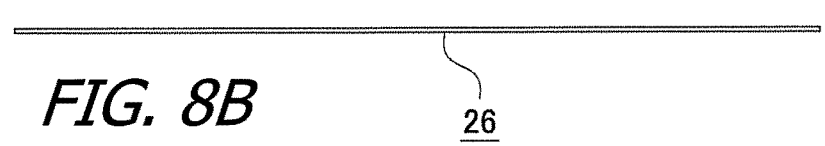

FIG. 8 is a view describing the structure of the supporting member, wherein FIG. 8A is a planar view, and FIG. 8B is a side view. The supporting member 26 supports the corneal endothelium layer 2e (shown by two dot chain line in the figure) as an example of the above-mentioned therapeutic substance.

The supporting member 26 is a thin sheet-type member having a thickness of about 0.08 mm for example. The supporting member 26 is preferably formed using fluorine resin, etc., so that a face on the side supporting at least the therapeutic substance, is a smooth face. The supporting member 26 is set in a planar developed state as shown in the figure, in a state free from an action of a force from outside. Further, the supporting member 26 can be easily deformed when an external force is added thereon.

The outer shape (planar shape) of the supporting member 26 is a tongue-like state having a rounded shape as a whole. The outer dimension of a rounded portion of the supporting member 26 may be set to the same dimension as the outer dimension of the corneal endothelium layer supported by the supporting member 26, or may be set to a dimension slightly larger or slightly smaller than the outer dimension of the corneal endothelium layer. Here, preferably "slightly" indicates a dimension range of 0.2 to 1.0 mm.

A part of the supporting member 26 is formed into an extending part 60 extended in the form of approximately a triangle in a direction of a center line of the supporting member 26 shown by one dot chain line in the figure. The extending part 60 is formed in consideration of not only the attachment of the supporting member 26 to the needle part 44, but also an easiness of the deformation of the supporting member 26 in a storing step described later. Two small holes 61a, 61b are formed on the extending part 60. Each one of the small holes 61a, 61b is formed in a state of passing through the supporting member 26 so as to avoid the position where the corneal endothelium layer 2e is supported on the supporting member 26. Specifically, two small holes 61a, 61b are formed to be positioned deviated to an extending side of the extending part 60, from a position where the corneal endothelium layer 2e is supported. Further, each one of the small holes 61a, 61b is formed with a specific interval provided between them, on the center line of the supporting member 26.

Connection Piece

Figure 9A:
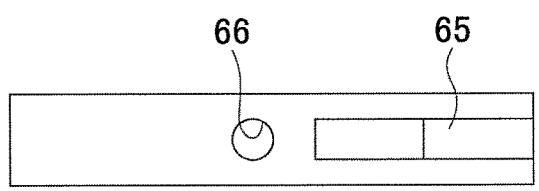
FIGS. 9A-9C are top, side and rear views of a connection piece.
Figure 9B:
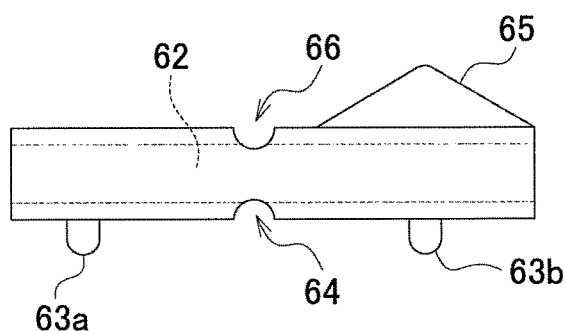
Figure 9C:
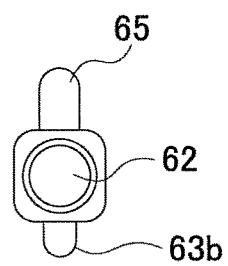

FIG. 9 is a view describing the structure of the connection piece, wherein FIG. 9(A) is a planar view, and FIG. 9(B) is a side view, and FIG. 9(C) is a view viewed from the rear end side. The connection piece 28 is a piece for fitting the supporting member 26 to the tip end (needle point portion) of the needle part 44. The connection piece 28 is a small piece made of resin such as polypropylene, and has an approximately a square outer shape with angles rounded viewed from the center axis direction. An insertion hole 62 is formed in the connection piece 28. The insertion hole 62 is a through hole with both ends opened. The insertion hole 62 is a hole for inserting the connection piece 28 into the tip end portion of the needle part 44. Therefore, the cross-sectional shape of the insertion hole 62 is a circular shape corresponding to the cross-sectional shape of the needle part 44. Further, the hole size of the insertion hole 62 is set corresponding to the outer dimension of the needle part 44, so that the connection piece 28 is fixed to the needle point portion by press-fitting for example when the tip end of the needle part 44 is inserted into the insertion hole 62.

Two protrusions 63a, 63b and a small hole 64 are formed on one of the two facing outer faces of the connection piece 28, and a mountain-like protrusion 65 and a small hole 66 are formed on the other outer face. The two protrusions 63a, 63b are provided corresponding to the two small holes 61a, 61b of the supporting member 26. Each of the protrusions 63a, 63b is formed into a cylindrical shape with a rounded tip end. The small holes 64, 66 are formed on the one outer face and the other outer face respectively, having the same center axis so as to pass through the outer faces. The protrusion 65 is formed on one end of the connection piece 28 in a longitudinal direction.

Structure of a Syringe Unit

As shown in FIG. 3, the syringe unit 22 is formed using a syringe 68 and a plunger 69. The syringe unit 22 functions to selectively cause a negative pressure and a positive pressure in the tubular part 31 of the nozzle member 23 through the through hole 41 of the valve member 27. The syringe 68 is formed into a cylindrical shape as a whole. An insertion part 70 is provided on the tip end of the syringe 68 in a protrusion state. A flange part 71 is provided on the rear end of the syringe 68.

The plunger 69 has a sliding part 72 made of rubber, and a rod part 73 supporting the sliding part 72. The sliding part 72 is provided on the tip end of the plunger 69. The sliding part 72 moves in the center axis direction of the syringe 68 by a retraction or pushing movement (operation) of the rod part 73 while being air-tightly adhered to the inner peripheral surface of the syringe 68. The rod part 73 is assembled into the syringe 68 so as to be inserted and extracted into/from the syringe 68 (so as to be slid into/from the syringe 68). The tip end side of the rod part 73 is inserted into the syringe 68 together with the sliding part 72. The rear end side of the rod part 73 is set in a protruding state from the syringe 68.

3. Method of Manufacturing the Therapeutic Instrument (Assembly Procedure)

Subsequently, the method of manufacturing a therapeutic instrument according to the first embodiment of the present invention will be described.

A therapeutic instrument 20 includes a body unit 21 and a syringe unit 22. The syringe unit 22 may be attachable and detachable to/from the needle member 25, and needs not to be a dedicated product, and may be provided as a generous purpose product (commercially available product). Here, as an example, the generous purpose product is used for the syringe unit 22. In this case, substantially the assembly step of the body unit 21 corresponds to the manufacturing step of the therapeutic instrument 20. A procedure of a specific assembly step of the body unit 21 will be described hereafter.

Figure 10A:
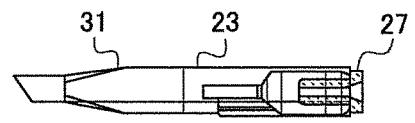
FIGS. 10A-10F are views showing an assembly step of a body unit, as an example of a method of manufacturing a therapeutic instrument according to a first embodiment of the present invention.
Figure 10B:
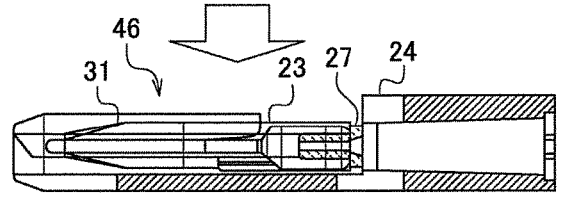

First, as shown in FIG. 10(A) and FIG. 10(B), the nozzle member 23 is assembled into the first holding part 46 of the holding member 24. Prior to the assembly, the valve member 27 is mounted on the nozzle member 23. Specifically, the valve member 27 is mounted on the nozzle member 23 so that a nose part 43 of the valve member 27 is inserted into the opening 35 of the tubular part 31 of the nozzle member 23 (see FIG. 4 and FIG. 5). Then, an engagement portion between the tubular part 31 and the valve member 27 is set in an air-tight state without allowing air leak, etc., or a state close thereto. Then, in this state, the valve member 27 is set in a state of being fixed to the nozzle member 23. The valve member 27 may be fixed to the nozzle member 23 simply by engagement (press-fitting) or may be fixed using an adhesive agent, etc., as needed.

Further, on assembling the nozzle member 23 this way, a blade part 37 of the nozzle member 23 (see FIG. 4) is received by the notch part 52 of the holding member 24 (see FIG. 7), and the tubular part 31 of the nozzle member 23 (see FIG. 4) is received by the nozzle receiving part 49 of the holding member 24 (see FIG. 7). The blade part 37 of the nozzle member 23 is received by the bottom surface 52a (see FIG. 7) of the notch part 52.

Figure 10C:
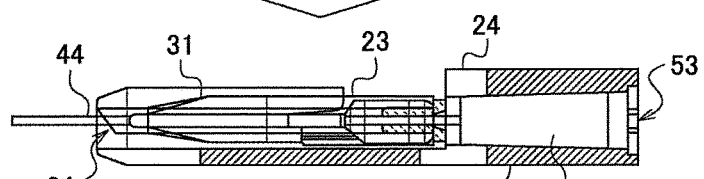

Next, as shown in FIG. 10(C), the needle member 25 is attached to the second holding part 47 of the holding member 24. Specifically, the needle part 44 of the needle member 25 is inserted from the fixing hole 53 (see FIG. 7) of the second holding part 47, and as described above, the needle part 44 is inserted into the through hole 41 of the valve member 27 (see FIG. 5) mounted on the nozzle member 23. Further, the base part 45 of the needle member 25 is engaged with the fixing hole 53 of the second holding part 47 of the holding member 24. At this time, the needle part 44 is set in a state of being engaged with a minimum diameter (d1) portion of the through hole 41. In this engagement state, the hole size d1 of the through hole 41 and the outer diameter of the needle part 44 are set so that a specific sliding friction resistance is generated in an engagement portion between the minimum diameter portion of the through hole 41 and the needle part 44. Further, the engagement portion between the through hole 41 and the needle part 44 is set in the air-tight state without air leak, etc., or the state close thereto. However, movement (sliding) of the needle part 44 is allowed.

Meanwhile, the tip end side of the needle part 44 of the needle member 25 is set in a state of passing through the valve member 27 to reach the inside of the tubular part 31, and thereafter protruding to outside from the opening 34 of the tubular part 31. Further, the base part 45 of the needle member 25 is set in a state of being fixed to the holding member 24 in a state of being fitted into the fixing hole 53 of the second holding part 47. Press-fitting by engagement or use of the adhesive agent, etc., may be acceptable as a more specific fixing means.

Figure 10D:
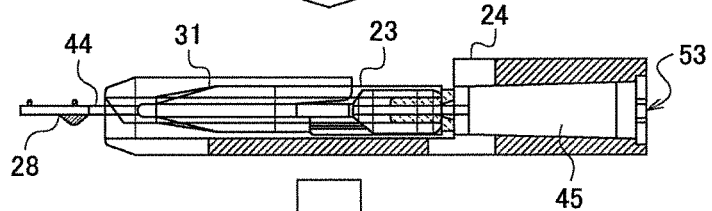

Next, as shown in FIG. 10(D), the connection piece 28 is fitted to the tip end of the needle part 44 of the needle member 25. Specifically, the tip end of the needle part 44 is inserted into the insertion hole 62 (see FIG. 9) of the connection piece 28. At this time, the connection piece 28 may be fixed to the needle part 44 by press-fitting by engagement, or may be fixed using the adhesive agent, etc., or may be fixed by caulk treatment utilizing a heat as will be described later. In any case, both are fixed so that the connection piece 28 is not moved in the center axis direction of the needle part 44.

Figure 10E:
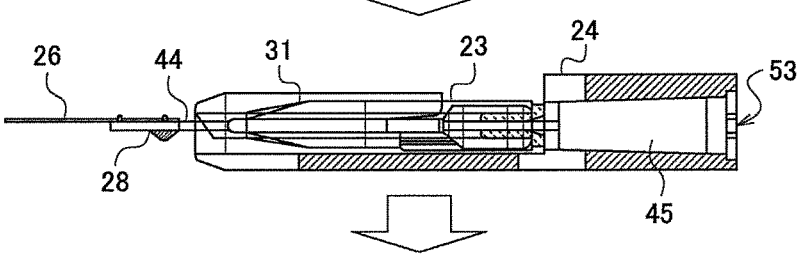

Next, as shown in FIG. 10(E), the supporting member 26 is fitted to the tip end of the needle part 44 using the connection piece 28. Specifically, two small holes 61a, 61b (see FIG. 8) of the supporting member 26 are respectively engaged with two protrusions 63a, 63b (see FIG. 9) of the connection piece 28.

Figure 10F:
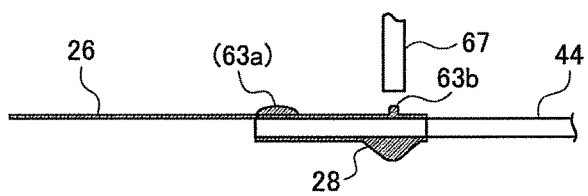

Next, as shown in FIG. 10(F), each of the protrusions 63a, 63b is melted by the heat of a heating tool 67, to thereby calk the supporting member 26. Thus, the supporting member 26 is set in a state of being fixed to the tip end portion of the needle part 44 using the connection piece 28.

As described above, the assembly of the body unit 21 is completed. Actually, when the therapeutic instrument 20 is used, the syringe unit 22 is mounted on the body unit 21 in this case. Specifically, the insertion part 70 of the syringe 68 is inserted into the base part 45 of the needle member 25 fixed to the rear end of the holding member 24.

4. Use Method of the Therapeutic Instrument

Subsequently, the use method of the therapeutic instrument according to the first embodiment of the present invention will be described. In the method of using the therapeutic instrument 20, first, explanation is given for a basic movement of the therapeutic instrument 20, and thereafter explanation is given for a using manner of the therapeutic instrument 20 in an actual corneal endothelium transplant surgery.

Basic Movement

The holding member 24 and the needle member 25 are moved relatively to the nozzle member 23. In this case, the needle member 25 is fixed to the holding member 24 and moved integrally with the holding member 24. Therefore, an operation of relatively moving the nozzle member 23 and the needle member 25, and an operation of relatively moving the nozzle member 23 and the holding member 24 are substantially the same operation.

First, when the nozzle member 23 and the holding member 24 are relatively moved, fingers (usually thumb and forefinger) of one hand are pressed against a pair of finger rest parts 32 provided on the nozzle member 23, to thereby support the nozzle member 23. Further, simultaneously, the outer peripheral surface of the second holding part 47 of the second holding member 24 is gripped and supported by fingers of the other hand. Then, a pressing force by either one of the hands or both hands is added toward the center axis direction of the therapeutic instrument 20, while maintaining the above-mentioned supporting state. Then, the nozzle member 23 and the holding member 24 are relatively moved in such a manner that the movement of the nozzle member 23 held by the holding member 24 is guided to the needle part 44 passing through the valve member 27.

When a range in which the nozzle member 23 and the holding member 24 are relatively moved in the center axis direction of the therapeutic instrument 20, is defined as a "relative moving range", one of the movement terminal ends and the other movement terminal end are regulated as follows in this relative moving range. Namely, one of the movement terminal ends is regulated by abutting of a pair of blade parts 37 formed on the nozzle member 23, on the abutting face 56 of the holding member 24. Thus, in a state that one of the movement terminal ends is regulated, the tip end of the needle part 44 and the supporting member 26 attached thereto, are in a state of protruding to outside of the nozzle member 23 through the opening 34 of the tubular part 31.

Meanwhile, the other movement terminal end is regulated by abutting of a pair of blade parts 37 formed on the nozzle member 23, on the tip end portion of the slit 50 of the holding member 24, when the nozzle member 23 and the holding member 24 are relatively moved. Thus, in a state that the other movement terminal end is regulated, the tip end of the needle part 44 and the supporting member 26 attached thereto are in a state of being drawn into the inner space 33 through the opening 34 of the tubular part 31. Further, in a stage slightly before abutting of the pair of blade parts 37, on the end portion of the slit 50 of the holding member 24, the pair of blade parts 37 move along the slit 50 while deforming (pushing-up) the beam parts 51 corresponding to the blade parts 37 respectively. At this time, a counterforce caused by the deformation of the beam part 51 works as a braking force against the movement of the pair of blade parts 37. The braking force described here, is generated by a difference between the thickness of the blade part 37 and the width of the slit 50.

In the explanation hereafter, when the nozzle member 23 and the holding member 24 are relatively moved, the movement of the blade part 37 of the nozzle member 23 in a direction separating from the abutting face 56 of the holding member 24, is defined as an advance movement of the nozzle member 23 with respect to the holding member 24. Meanwhile, reversely, the movement of the blade part 37 of the nozzle member 23 in a direction of approaching the abutting face 56 of the holding member 24, is defined as a retreat movement of the nozzle member 23 with respect to the holding member 24. Therefore, when the nozzle member 23 is advanced, the blade part 37 approaches the tip end portion of the slit 50, and when the nozzle member 23 is retreated, the blade part 37 is separated from the tip end portion of the slit 50.

In a state that the nozzle member 23 is most advanced by the advance movement, the tip end of the needle part 44 and the supporting member 26 are set in a state of being retracted into the tubular part 31. Further, in a state that the nozzle member 23 is most retreated by the retreat movement, the tip end of the needle part 44 and the supporting member 26 are set in a state of protruding to outside of the tubular part 31.

Further, in either case of the advance movement and the retreat movement, the sliding friction resistance works in a contact portion between the through hole 41 of the valve member 27 and the needle part 44 engaged with the through hole 41, to a degree not excessively inhibiting the relative movement of the nozzle member 23 and the holding member 24. By the function of the sliding friction resistance, the nozzle member 23 and the holding member 24 are stopped at an arbitrary position in the relative moving range, and such a stop state can be maintained.

Use Method

When being roughly classified in time series, the use method of the therapeutic instrument 20 is classified into a storing step and a pushing step. Each step will be specifically described hereafter.

Storing Step

Figure 11A:
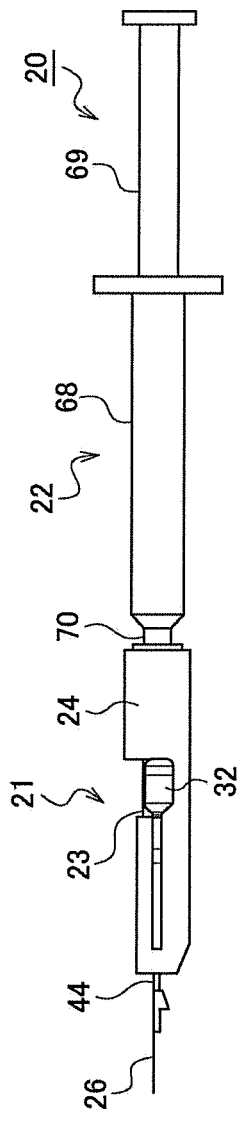
FIGS. 11A-11D are side views (first views) showing a use method of the therapeutic instrument according to the first embodiment of the present invention.

First, as shown in FIG. 11(A), the nozzle member 23 is set in a most retreated state, as a state of the body unit 21. Then, the tip end of the needle part 44 is protruded from the tip end of the nozzle member 23, and therefore the supporting member 26 fitted thereto is set in a planar developed state. In this state, an inside of the syringe 68 of the syringe unit 22 is filled with medical water in advance. Filling operation of the medical water is performed, for example, in such a manner that the medical water is put in a container, etc., and the insertion part 70 of the syringe 68 is prepared by putting it in the medical water, and plunger 69 is operated so as to be retracted therein, before the syringe unit 22 is mounted on the body unit 21. Thus, the medical water is sucked into the syringe 68 through the insertion part 70. Then, in a state of sucking a specific amount of the medical water into the syringe 68 by retraction of the plunger 69, the syringe unit 22 is mounted on the body unit 21.

Incidentally, the medical water described in this specification is the water suitable for a medical use, such as sterilization-treated water or physiological saline. The medical water used for filling the syringe 68 has an auxiliary function when the inside of the tubular part 31 is set in a negative pressure or a positive pressure. However, gas such as air can also be used instead.

Figure 11B:
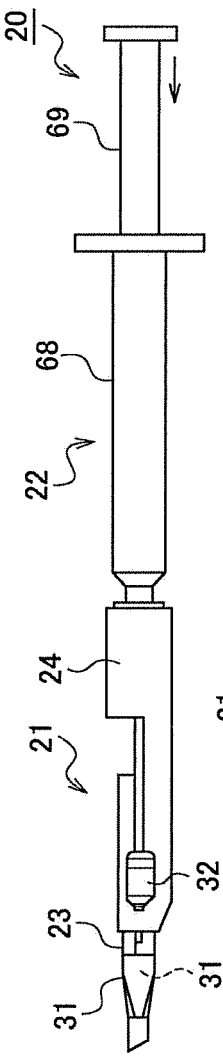

Next, as shown in FIG. 11(B), after the advance movement of the nozzle member 23, the inside of the tubular part 31 of the nozzle member 23 is filled with the medical water. In this case, by allowing the nozzle member 23 to be set in a most advanced state with respect to the holding member 24, the supporting member 26 is completely retracted into the space 33 of the tubular part 31. Then, the supporting member 26 is set in a state of being stored in the tubular part 31, while being deformed into a roll-shape. By pushing a specific portion of the plunger 69 of the syringe unit 22 while maintaining such a stored state (drawn state), the inside of the tubular part 31 of the nozzle member 23 is filled with the medical water.

Here, as described above, in the middle of the advance movement of the nozzle member 23, the protrusion 65 is brought into contact with the opening 34 of the tubular part 31, and the supporting member 26 is pushed to the opposite side of the opening 34. At this time, the supporting member 26 is deformed to be gradually rounded by receiving an outer force caused by such a contact with the opening 34. Finally the supporting member 26 is retracted into the space 33 of the tubular part 31 in a state of being deformed into a roll-shape (in a state of being rounded into an arc shape). An retracting operation in this stage is performed so that the supporting member 26 protruded from the tip end of the tubular part 31 and set in a free state (open state), is shaped into a form easy to be curled.

Figure 11C:
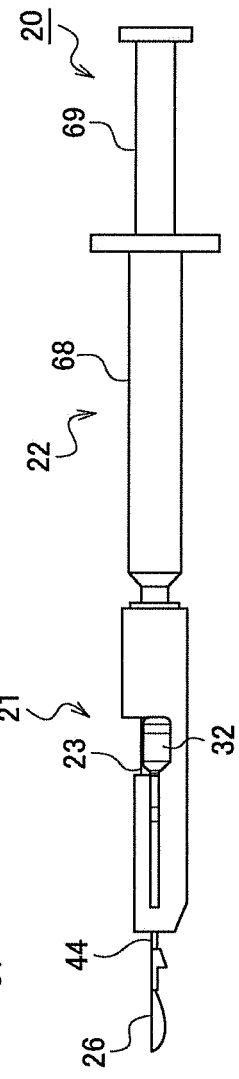

Next, as shown in FIG. 11(C), the nozzle member 23 is retreated. In this case, by making the nozzle member 23 most retreated with respect to the holding member 24, the supporting member 26 is protruded from the tip end of the tubular part 31. At this time, at least a part of the medical water with which the inside of the tubular part 31 is filled as described above, is discharged by the retreat movement of the nozzle member 23. Further, the supporting member 26 is set in a state that it is shaped into a slightly curved shape.

Figure 11D:
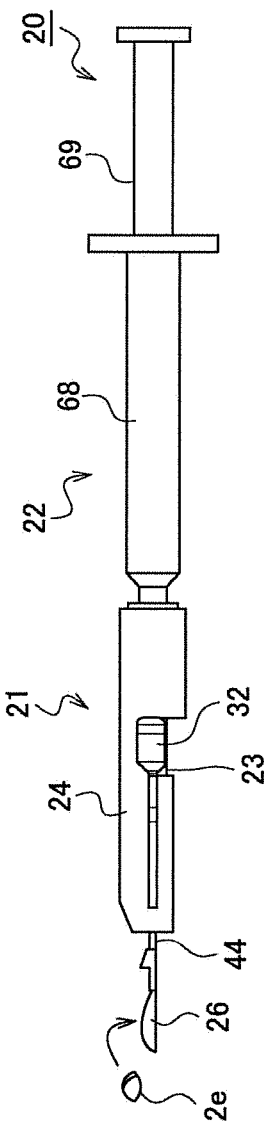

Next, as shown in FIG. 11(D), the therapeutic instrument 20 is vertically inverted (rotated by 180 degrees), and thereafter a previously prepared corneal endothelium layer 2e is placed on the supporting member 26. Then, a state as shown in FIG. 12(A) is obtained.

Next, as shown in FIG. 12(B), a liquid 75 is delivered to the corneal endothelium layer 2e. Specifically, for example, an injector 74 with an inside of the syringe filled with liquid, is used to drop the liquid 75 onto the corneal endothelium layer 2e. As the liquid 75 delivered to the corneal endothelium layer 2e, the above-mentioned medical water may be used, and a substance having higher viscoelasticity than that of the medical water (viscoelastic substance) is more preferable. Further, hyaluronic acid can be given as a preferable example of the viscoelastic substance.

When the liquid containing the viscoelastic substance such as hyaluronic acid, is delivered to the corneal endothelium layer 2e, the surface of the corneal endothelium layer 2e is coated and protected by a viscoelastic property of the liquid. Therefore, a damage (such as a damage of a cell) of the corneal endothelium layer 2e by the corneal endothelium transplant surgery can be reduced.

Next, as shown in FIG. 12(C), the nozzle member 23 is slowly advanced so as not to add an excessively large load on the corneal endothelium layer 2e on the supporting member 26. Then, as shown in FIG. 13(A), the supporting member 26 is brought into contact with the opening 34 of the tubular part 31 in the middle of the advance movement of the nozzle member 23, to thereby gradually deform the supporting member 26 into U-shape, and similarly deform the corneal endothelium layer 2e in the same way.

At this time, as shown in FIG. 13(B), the corneal endothelium layer 2e supported by the supporting member 26 begins to enter into the space 33 of the tubular part 31 together with the supporting member 26. In this state, the advance movement of the nozzle member 23 is stopped once. Next, a specific portion of the plunger 69 of the syringe unit 22 is retracted (FIG. 13(B)). Next, the nozzle member 23 is advanced until the blade part 37 of the nozzle member 23 (see FIG. 4) abuts on the tip end portion of the slit 50 (see FIG. 7) of the holding member 24 (FIG. 13(C)). The reason for retracting the corneal endothelium layer 2e in a stop state once, is that when the corneal endothelium layer 2e is retracted together with the supporting member 26, in many cases, the corneal endothelium layer 2e is not deformed completely integrally with the supporting member 26, and a part of the corneal endothelium layer 2e protrudes from the supporting member 26 or floats from the supporting member 26, thus making it impossible to satisfactorily retract the corneal endothelium layer 2e. Even if the corneal endothelium layer 2e can be retracted, it is hardly pushed out in many cases. The reason is considered as follows. Namely, when the corneal endothelium layer 2e is retracted together with the supporting member 26, the corneal endothelium layer 2e and the supporting member 26 cannot be uniformly brought into contact with each other, thus adding a strong load on a part of the corneal endothelium layer 2e, and causing a clogging thereby. Meanwhile, the retraction by the negative pressure is considered to urge a uniform contact between the corneal endothelium layer 2e and a member in contact with the corneal endothelium layer 2e.

Thus, the corneal endothelium layer 2e is set in a state of being completely stored inside of the tubular part 31 (FIG. 13(C)). Also, the tip end side of the tubular part 31 is set in a state of being closed by the liquid 75 which is sucked together with the corneal endothelium layer 2e.

As described above, the storing step is completed. In an actual corneal endothelium layer transplant surgery, a surgical operation for removing and inserting the corneal endothelium layer, and a removing operation of the corneal endothelium layer afflicted with a corneal disorder, are applied to an eyeball being a transplant object, before the above-mentioned storing step. Further, slit-like incisions are formed at two places of the corneal portion by the surgical operation. Then, by constantly delivering a suitable amount of the medical water from one of the incisions, the corneal portion is maintained in a cup-shaped protrusion shape.

Pushing Step

In the pushing step, as shown in FIG. 14(A), the therapeutic instrument 20 after end of the storage of the corneal endothelium layer 2e by the above-mentioned storing step, is approached to the affected part of an eyeball 1 (a transplant part of the corneal endothelium layer). At this time, the therapeutic instrument 20 is approached to the eyeball 1, in a state that the opening 34 obliquely formed on the tip end of the tubular part 31 is faced toward the eyeball 1 side.

Next, as shown in FIG. 14(B), the tip end of the nozzle member 23 is inserted into the corneal portion of the eyeball 1, with the therapeutic instrument 20 suitably inclined. Specifically, the beak part 36 (see FIG. 4) of the nozzle member 23 is inserted into the other incision formed on the corneal portion, by the above-mentioned incision surgery.

Next, while maintaining a state shown in FIG. 14(C) with the therapeutic instrument 20 gripped by one hand, the plunger 69 is pushed by the other hand. Then, the positive pressure acts in the space 33 in the tubular part 31 by push of the plunger 69. By receiving the positive pressure, the corneal endothelium layer 2e in the tubular part 31 is pushed to the outside of the tubular part 31 together with the liquid 75. Namely, the corneal endothelium layer 2e is discharged from the opening 34 at the tip end of the beak part 36 together with the liquid 75.

Thus, the corneal endothelium layer 2e is inserted into an anterior chamber 5 (see FIG. 1).

5. Effect of a First Embodiment

According to the therapeutic instrument according to the first embodiment of the present invention, the following effect can be obtained.

In the therapeutic instrument 20 according to the first embodiment of the present invention, the retracting operation of the plunger 69 of the syringe unit 22 is performed for storing the corneal endothelium layer 2e in the tubular part 31 of the nozzle member 23, to thereby cause the negative pressure to act in the tubular part 31. Then, by utilizing this negative pressure, the corneal endothelium layer 2e is sucked into the tubular part 31. Further, when the corneal endothelium layer 2e is delivered to the affected part of the eyeball 1, the pushing operation of the plunger 69 of the syringe unit 22 is performed to thereby cause the positive pressure to act in the tubular part 31, and by utilizing this positive pressure, the corneal endothelium layer 2e is pushed-out to the outside of the tubular part 31.

Thus, when the corneal endothelium layer 2e is stored in the tubular part 31 of the nozzle member 23, the corneal endothelium layer 2e can be suitably and surely stored in the space 33 in the tubular part 31, for example compared with a case that the corneal endothelium layer 2e is stored in the tubular part 31 only by the retraction movement of the needle part 44 which is performed by the relative movement of the nozzle member 23 and the holding member 24.

As a result, when the pushing operation of the plunger 69 is performed, the corneal endothelium layer 2e can be smoothly and suitably pushed-out to the outside of the tubular part 31. Therefore, when the transplant surgery of the corneal endothelium layer is performed, the corneal endothelium layer 2e can be suitably inserted into a corneal part being a transplant object. Further, when the liquid 75 is delivered to the corneal endothelium layer 2e, the retracting operation of the corneal endothelium layer 2e is promoted by an existence of the liquid 75 in a case of the retraction of the corneal endothelium layer 2e by causing the negative pressure to act in the tubular part 31. Moreover, when the corneal endothelium layer 2e is pushed-out by causing the positive pressure to act in the tubular part 31 after it is stored in the tubular part 31, a push-out action is promoted by the existence of the liquid 75. Therefore, reliability of the transplant surgery of the corneal endothelium layer can be further increased. However, in realizing the present invention, the retraction by the action of the negative pressure or the push-out by the action of the positive pressure, can be performed, even if not previously delivering the liquid 75 to the corneal endothelium layer 2e.

Further, in performing the pushing operation of the plunger 69, the supporting member 26 is maintained in a state of being stored in the nozzle member 23, because the needle part 44 is not moved. Therefore, a degree of invasion to a transplant part can be considerably reduced, compared with a case of using the therapeutic instrument which needs to be inserted into the corneal together with a substance other than a transplant piece.

Further, the first embodiment of the present invention has a structure in which the corneal endothelium layer 2e placed on the supporting member 26 at the tip end of the needle part 44, is retracted into the tubular part 31 together with the supporting member 26, by the relative movement of the nozzle member 23 and the holding member 24. Therefore, as a preparation for retracting the corneal endothelium layer 2e by the negative pressure, a damage (damage of the cell, etc.,) of the corneal endothelium layer 2e can be reduced, for example compared with a case that the corneal endothelium layer 2e is clipped by tweezers, etc., to insert it into a portion of the opening 34 of the tubular part 31.

Further, the supporting member 26 is protruded to the outside of the tubular part 31 before the corneal endothelium layer 2e is stored in the tubular part 31, so that the corneal endothelium layer 2e can be placed and supported thereon. In addition, when the corneal endothelium layer 2e is stored in the tubular part 31 from this state, the corneal endothelium layer 2e supported by the supporting member 26 can be retracted into the tubular part 31 together with the supporting member 26. Therefore, there is no necessity for inserting the corneal endothelium layer 2e into the tubular part 31, using an instrument different from the therapeutic instrument 20.

Further, when the tip end of the needle part 44 is retracted into the tubular part 31 from the state of protruding into the tubular part 31, the corneal endothelium layer 2e supported by the supporting member 26 is deformed into a roll shape together with the supporting member 26. Therefore, the corneal endothelium layer 2e and the liquid 75 can be stored in the tubular part 31 together.

Further, in the above-mentioned storing step and pushing step, the damage (such as a damage of the cell, etc.,) of the corneal endothelium layer 2e can be reduced when taking in and out operation is performed into/from the tubular part 31, by delivering the liquid of the viscoelastic substance such as hyaluronic acid, to the corneal endothelium layer 2e in advance.

Further, in the storing step and the pushing step, the second holding part 47 of the holding member 24, and a pair of finger rest parts 32 of the nozzle member 23, are gripped by fingers respectively, to thereby relatively move the nozzle member 23 and the needle member 25. Therefore, operability of the therapeutic instrument 20 becomes satisfactory, compared with a case that, for example, the body portion (tubular part 31) of the nozzle member 23 and the base part 45 of the needle member 25 are operated by being gripped by fingers respectively.

Further, the first embodiment has a structure as follows: Namely, the movement terminal end position for performing the relative movement of the nozzle member 23 and the needle member 25, is regulated by the slit 50 by the beam 51 of the holding member 24, and the abutting face 56 of the holding member 24 respectively. Therefore, in the relative moving range of the nozzle member 23 and the needle member 25, excessive retraction can be prevented, and the position of the supporting member 26 can be stabilized at the time of completion of the retraction, for example when the tip end of the needle part 44 and the supporting member 26 are retracted into the tubular part 31.

6. Second Embodiment

Structure of the Therapeutic Instrument

FIG. 15 to FIG. 17 are views showing the structure and a use method of the therapeutic instrument according to a second embodiment of the present invention. The therapeutic instrument 20 of the second embodiment is different from the first embodiment particularly in the following point, compared with the above-mentioned first embodiment. Namely, the first embodiment has a structure such that the relative movement of the nozzle member 23 and the needle member 25 is assisted by the holding member 24. However, the second embodiment does not have the structure including the holding member 24 and the needle member 25.

Specifically, as shown in FIG. 15(A), the therapeutic instrument 20 is constituted of the nozzle member 23 and the syringe unit 22, and the syringe unit 22 is directly brought into contact with the rear end portion of the nozzle member 23. A connecting hole (not shown) corresponding to an outer diameter of the insertion part 70 of the syringe 68 is formed on the rear end portion of the nozzle member 23 instead of the above-mentioned opening 35 and valve member 27, and the insertion part 70 is inserted into this connecting hole coaxially. The connecting hole described here corresponds to the "communication part" communicated with the space of the tubular part 31 of the nozzle member 23.

Use Method of the Therapeutic Instrument

Next, explanation is given for the use method of the therapeutic instrument 20 having the above-mentioned structure. In this embodiment as well, explanation is given by classifying the steps into the storing step and the pushing step.

Storing Step

First, as a previous preparation work, the inside of the syringe 68 of the syringe unit 22 is filled with the medical water, and thereafter the insertion part 70 of the syringe 68 is inserted into the hole at the rear end portion of the nozzle member 23, to thereby connect the nozzle member 23 and the syringe unit 22. Next, the inside of the tubular part 31 of the nozzle member 23 is filled with the medical water by pushing a specific portion of the plunger 69 of the syringe unit 22.

Meanwhile, as shown in FIG. 15(B) and FIG. 15(C), the corneal endothelium layer 2e is set in a delivery instrument 76 different from the therapeutic instrument 20. A receiving part 77 curved into a roll-shape is provided on the tip end portion of the delivery instrument 76. When the corneal endothelium layer 2e is set in the receiving part 77, the corneal endothelium layer 2e is placed on the receiving part 77 of the delivery instrument 76, and thereafter the viscoelastic liquid 75 made of the viscoelastic substance is dropped (delivered) onto the corneal endothelium layer 2e using the injector 78. Then, the corneal endothelium layer 2e is deformed into a roll-shape following a concave surface shape of the receiving part 77, resulting in forming a state of accumulating the liquid 75 in an inner peripheral side portion. Hyaluronic acid is preferably used as the liquid 75 delivered to the corneal endothelium layer 2e, similarly to the first embodiment.

Figure 16A:
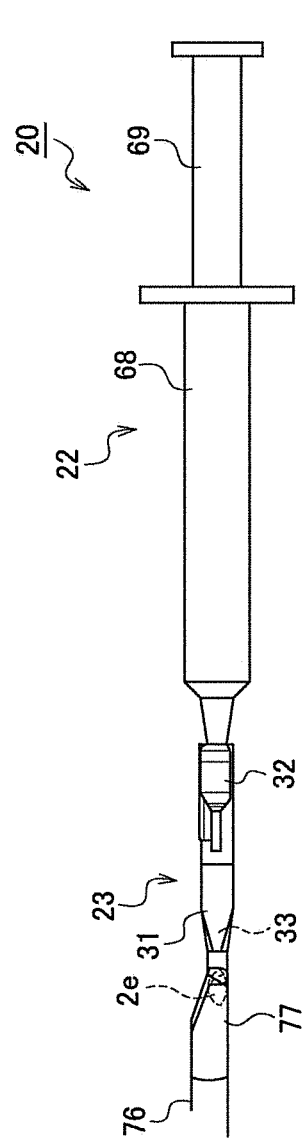
FIGS. 16A-16C are side views (second views) showing the structure and the use method of the therapeutic instrument according to the second embodiment of the present invention.
Figure 16B:
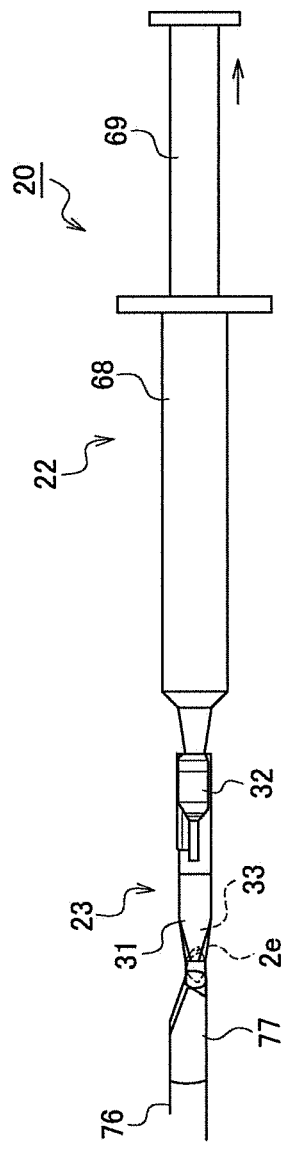
Figure 16C:
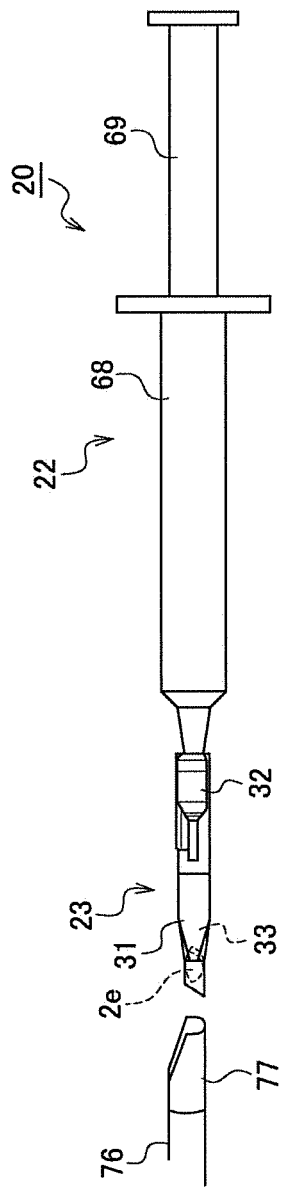

Next, as shown in FIG. 16(A), the tip end portion of the receiving part 77 of the delivery instrument 76 is inserted into the opening 34 of the nozzle member 23 (see FIG. 4). At this time, at least a part of the corneal endothelium layer 2e is set in a state of being inserted into the tubular part 31 of the nozzle member 23. Therefore, a specific portion of the plunger 69 of the syringe unit 22 is retracted into the tubular part 31, while maintaining the above insertion state. Then, similarly to the first embodiment, air in the tubular part 31 is sucked through the needle part 44, thus causing the negative pressure to act in the tubular part 31. By such an action of the negative pressure, the corneal endothelium layer 2e is sucked into the tubular part 31 together with the liquid 75. As a result, as shown in FIG. 16(C), after passing through a state of being sucked as shown in FIG. 16(B), the corneal endothelium layer 2e is set in a completely stored state in the tubular part 31. Further, the tip end side of the tubular part 31 is set in a closed state by the liquid 75 sucked into the tubular part 31 together with the corneal endothelium layer 2e.

The storing step is completed as described above. In the actual corneal endothelium layer transplant surgery, the surgical operation for removing and inserting the corneal endothelium layer, and a surgery for removing the corneal endothelium layer afflicted with the corneal disorder, are applied to the eyeball being a transplant object, before the above-mentioned storing step. Further, the slit-like incisions are formed at two places of the corneal portion by this surgical operation. Then, by constantly delivering a suitable amount of the medical water from one of the incisions, the corneal portion is maintained in a cup-shaped protrusion shape.

Pushing Step

Figures 17A, 17B, 17C:
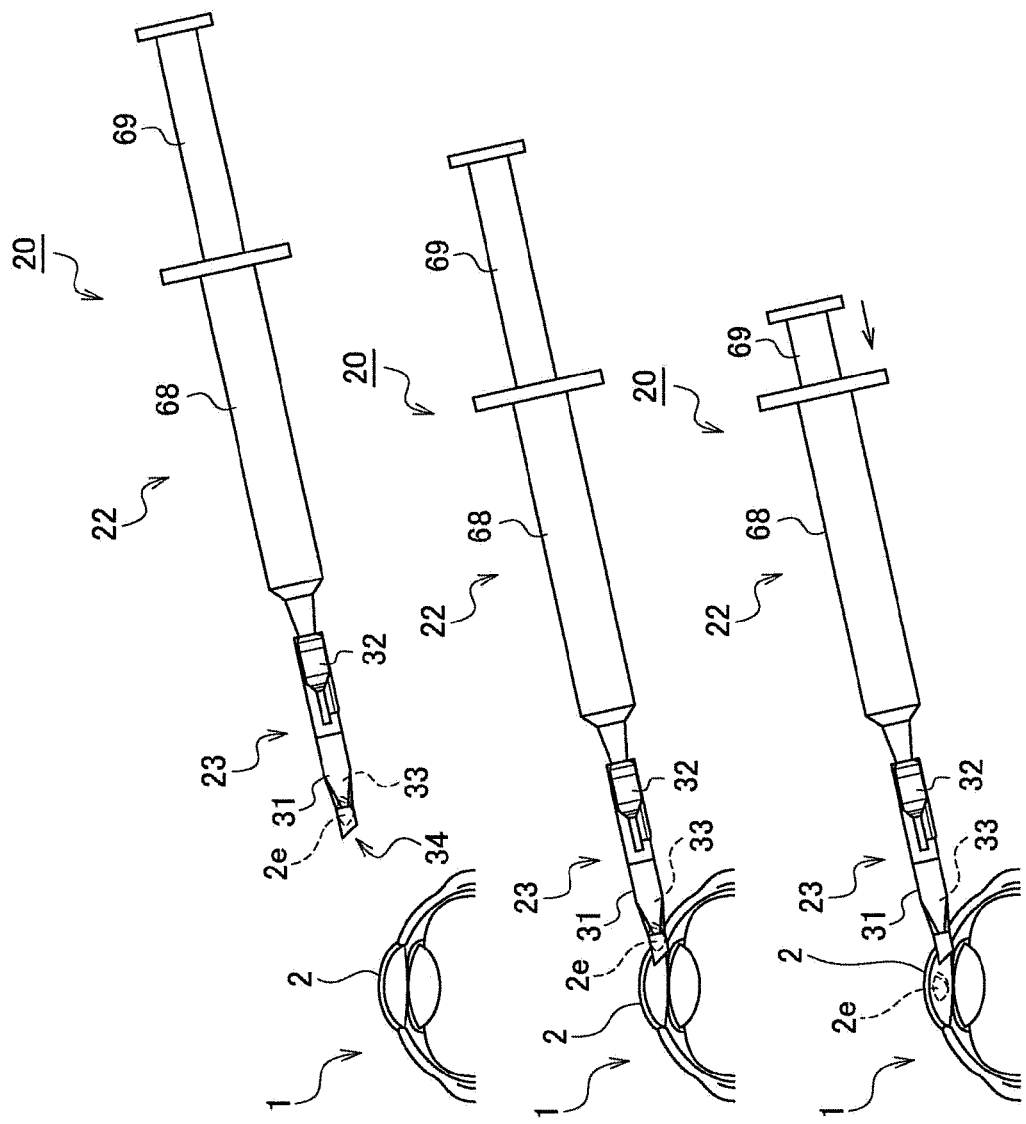
FIGS. 17A-17C are side views (third views) showing the structure and the use method of the therapeutic instrument according to the second embodiment of the present invention.

In the pushing step, as shown in FIG. 17(A), the therapeutic instrument 20 after end of storing the corneal endothelium layer 2e by the above-mentioned storing step, is approached to the affected part (transplant part of the corneal endothelium layer) of the eyeball 1. At this time, the opening 34 which is obliquely formed on the tip end of the tubular part 31, is faced toward the eyeball 1, and in this state, the therapeutic instrument 20 is approached to the eyeball 1.

Next, as shown in FIG. 17(B), the tip end of the nozzle member 23 is inserted into the corneal portion of the eyeball 1 in a state that the therapeutic instrument 20 is suitably inclined. Specifically, the beak part 36 of the nozzle member 23 (see FIG. 4) is inserted into the other incision which is formed on the corneal portion by the above-mentioned surgical operation.

Next, while maintaining a state shown in FIG. 17(C) with the nozzle member 23 gripped by one hand, the plunger 69 is pushed by the other hand. Then, the positive pressure acts in the space 33 in the tubular part 31 by push of the plunger 69. By receiving the positive pressure, the corneal endothelium layer 2e in the tubular part 31 is pushed to outside of the tubular part 31 together with the liquid 75. Namely, the corneal endothelium layer 2e is discharged from the opening 34 at the tip end of the beak part 36 together with the liquid 75. Further, when the plunger 69 is pushed as described above, the medical water with which the inside of the syringe 68 is filled, is delivered through the needle part 44. The delivered medical water is discharged from the opening 34 at the tip end of the beak part 36, together with the corneal endothelium layer 2e.

Thus, the corneal endothelium layer 2e is inserted (delivered) into the anterior chamber 5 (see FIG. 1).

In this embodiment, the syringe 68 is filled with the medical water, and such medical water is discharged together with the corneal endothelium layer 2e by push of the plunger 69. However, the inside of the syringe 68 may also be filled with the viscoelastic substance such as hyaluronic acid instead of the medical water. In this case, the viscoelastic substance is discharged together with the corneal endothelium layer 2e by push of the plunger 69. Therefore, when the viscoelastic substance is delivered from the tip end of the needle part 44 in a state that a part or the whole part of the corneal endothelium layer 2e remains in the space 33 in the tubular part 31 for example, a resistance that works on a contact interface between the corneal endothelium layer 2e and the viscoelastic substance, becomes larger than a case of using the medical water. Therefore, an action of pushing out the corneal endothelium layer 2e to the outside of the tubular part 31 becomes strong compared with a case of using the above-mentioned medical water, due to a property of the viscoelastic substance. Accordingly, the corneal endothelium layer 2e can be surely pushed out to the outside of the tubular part 31. Regarding this point, the same thing can be said for other embodiment.

7. Effect of the Second Embodiment

Thus, in the used therapeutic instrument 20, an effect similar to the effect of the first embodiment can be obtained, excluding the effect related to the holding member 24 and the needle member 25. Further, the second embodiment does not include the holding member 24 and the needle member 25 in constitutional elements, thus simplifying the structure of the therapeutic instrument 20. Therefore, the therapeutic instrument 20 can be provided at a low cost.

8. Third Embodiment

Figures 18A, 18B:
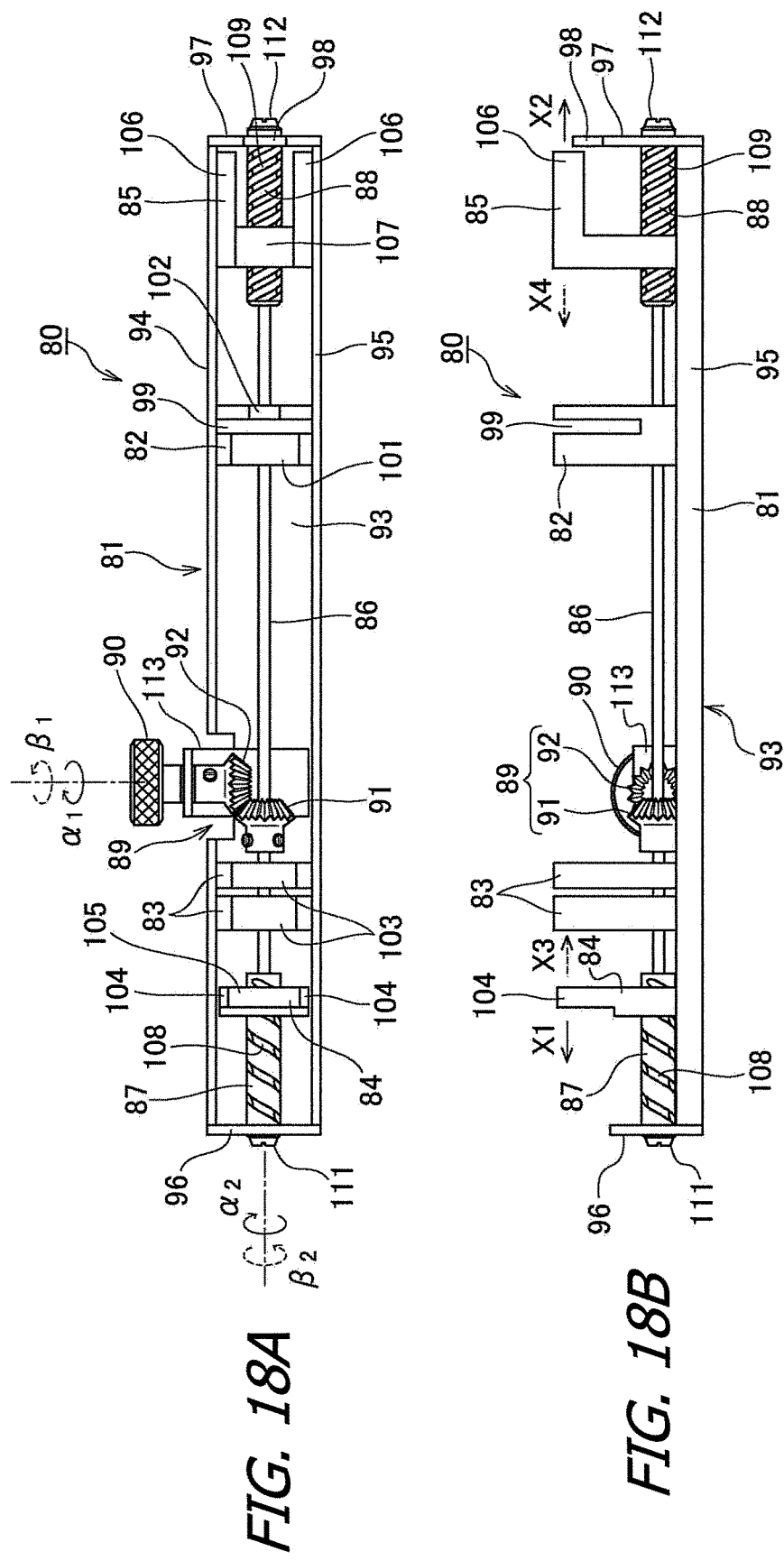
FIGS. 18A-18B are top and side views of an attachment according to a third embodiment of the present invention.

FIG. 18 shows the structure of an attached jig according to a third embodiment of the present invention, wherein FIG. 18(A) is a planar view of the attachment, and FIG. 18(B) shows a side view of the attachment, respectively.

There are two cases as an attachment 80 shown in the figure, depending on an interpretation of the present invention. As one of the cases, the attachment 80 is regarded as one of the elements (one constitutional element) constituting the therapeutic instrument according to the present invention (called a "first case" hereafter). As the other case, the attachment 80 is regarded as an independent existence different from the therapeutic instrument according to the present invention (called a "second case" hereafter).

In the first case, the attachment 80 is an instrument constituting the "therapeutic instrument" of the present invention, together with the therapeutic instrument 20, as the attachment (attached unit) attached to the therapeutic instrument 20 according to the first embodiment. In other words, according to the first case, the "therapeutic instrument" of the present invention includes both of the therapeutic instrument 20 of the first embodiment and the attachment 80 simultaneously.

In the second case, the attachment 80 is used in combination with the therapeutic instrument 20 of the first embodiment. In other words, according to the second case, the attachment 80 exists independently or separately from the therapeutic instrument 20 of the first embodiment. In this case, the attachment 80 corresponds to an instrument for handling the therapeutic instrument 20 of the first embodiment.

Structure of the Attachment

The attachment 80 corresponds to the "attached unit" for causing the negative pressure to act in the tubular part 31 by the relative movement of the nozzle member 23 and the needle member 25. Further, more specifically, the attachment 80 inter-connectedly performs an operation of relatively moving the nozzle member 23 and the needle member 25, and an operation of a pressure generator. The attachment 80 is mainly constituted of a base member 81; a positioning member 82; a receiving member 83; a first mover 84; a second mover 85; a driving shaft 86; a first grooved member 87; a second grooved member 88; a driving force transmission mechanism 89, and a knob 90. Further, the driving force transmission mechanism 89 is constituted of a first gear 91 and a second gear 92. These constitutional members are constituted, for example using a metal material such as stainless. However, the material is not limited thereto, and a part or the whole part of the constitutional member can be made of a resin material.

The syringe unit 22 corresponds to the "pressure generator", and a rod part 73 of the syringe unit 22 corresponds to a "movable part of the pressure generator". Moreover, the attachment 80 corresponds to an "attached unit", and the first mover 84 corresponds to a "first moving unit", and the second mover 85 corresponds to a "second moving unit" respectively. Further, a "driving unit for concurrently moving the first moving unit and the second moving unit" is constituted of the driving shaft 86; the first grooved member 87; the second grooved member 88; the driving force transmission mechanism 89; and the knob 90, etc. Each constitutional member will be sequentially described hereafter.

The base member 81 integrally includes a rectangular bottom plate part 93 extending in one direction with a fixed width; side plate parts 94, 95 vertically rising from two long side parts of the bottom plate part 93; and end plate parts 96, 97 vertically rising from two short side parts of the bottom plate part 93. A protrusion 98 is integrally formed on the end plate part 97. The protrusion 98 protrudes upward in a middle part of the end plate part 97 in a width direction, to thereby avoid a positional interference (contact) with the second mover 85 as will be described later. A recessed groove is formed on the protrusion 98, having approximately a V-shape viewed from a longitudinal direction of the base member 81. The recessed groove is a part for receiving the rod part 73 of the plunger 69 from below.

The positioning member 82 performs positioning and supports the therapeutic instrument 20 of the first embodiment (including the plunger 69 mounted on the body unit 21). The positioning member 82 is fixed to an upper surface of the bottom plate part 93 of the base member 81 by screwing for example. A slit part 99 is integrally formed on the positioning member 82. The slit part 99 is formed in parallel to a short direction of the base member 81. The slit part 99 is a part with which the flange part 71 (see FIG. 3) of the plunger 69 is engaged. Further, a syringe receiving part 101 and a rod receiving part 102 are integrally formed on the positioning member 82. The syringe receiving part 101 and the rod receiving part 102 are formed on one side and the other side of the positioning member 82, with the slit part 99 interposed between them. The syringe receiving part 101 is a part for receiving the syringe 68 of the syringe unit 22, and is formed in a state of being recessed into a U-shape viewed from the longitudinal direction of the base member 81. The rod receiving part 102 is a part for receiving the rod part 73 of the syringe unit 22, and is formed in a state of being recessed into the U-shape viewed from the longitudinal direction of the base member 81.

The receiving member 83 is a member for receiving and supporting the body unit 21 of the therapeutic instrument 20 from below. The receiving member 83 is fixed to the upper surface of the bottom plate part 93 of the base member 81 by screwing, etc., for example. A unit receiving part 103 is integrally formed on the receiving member 83. The unit receiving part 103 is formed in a state of being recessed into the U-shape viewed from the longitudinal direction of the base member 81. In an example shown in the figure, the receiving member 83 is constituted of two members divided in the longitudinal direction of the base member 81. However, the structure of the receiving member 83 is not limited thereto, and the receiving member 83 may be constituted of only one of the two members. Further, preferably planar parts 57 (see FIG. 7) called so-called D-cuts are formed at two places of both sides on the outer peripheral surface of the holding member 24 constituting the body unit 21, and each planar part 57 is brought into contact with mutually opposed two side wall faces of the receiving member 83, to thereby suppress an unnecessary rotation of the body unit 21.

The first mover 84 is provided movably on the bottom plate part 93 of the base member 81. The first mover 84 is disposed between the receiving member 83 and the end plate part 96 in a rotation axis direction of the driving shaft 86. The first mover 84 moves in the longitudinal direction of the base member 81, guided by two side plate parts 94, 95 of the base member 81. Two pressers 104 and an escape part 105 are integrally formed on the first mover 84. Two pressers 104 are disposed in a state of being opposed to each other in the short direction of the base member 81. The escape part 105 is formed between the two pressers 104 in the short direction of the base member 81. The escape part 105 is a part for avoiding a contact (positional interference) with the body unit 21, when the therapeutic instrument 20 is set in the attachment 80. Further, a hole part not shown is formed on the first mover 84, and a first engagement pin (not shown) protruded through the hole part, is assembled into the first mover 84. Particularly the hole part is formed having a slightly larger (for example, about 0.5 to 1.0 mm larger) inner diameter than an outer diameter of the first grooved member 87. The first engagement pin is engaged with a spiral groove 108 formed on the first grooved member 87 as will be described later.

The second mover 85 is provided movably on the bottom plate part 93 of the base member 81. The second mover 85 is disposed between the positioning member 82 and the end plate part 97 in the rotation axis direction of the driving shaft 86. The second mover 85 is formed into an L-shape viewed from the short direction of the base member 81. The second mover 85 moves in the longitudinal direction of the base member 81 guided by two side plate parts 94, 95 of the base member 81. Two pressers 106 and an escape part 107 are integrally provided on the second mover 85. The two pressers 106 are disposed in a state of being opposed to each other in the short direction of the base member 81. The escape part 107 is formed between the two pressers 106 in the short direction of the base member 81. The escape part 107 is a part for avoiding the contact (positional interference) with the plunger 69 of the syringe unit 22, when the therapeutic instrument 20 is set in the attachment 80. Further, a hole part not shown is formed on the second mover 85, and a second engagement pin (not shown) protruded through the hole part is assembled into the second mover 85. Particularly the hole part is formed having a slightly larger (for example, about 0.5 to 1.0 mm larger) inner diameter than an outer diameter of the second grooved member 88. The second engagement pin is engaged with a spiral groove 109 formed on the second grooved member 88 as will be described later.

The driving shaft 86 is rotatably supported by the positioning member 82 and the receiving member 83. More specifically, the driving shaft 86 is rotatably supported in a state of being inserted into a shaft supporting hole (not shown) provided on the positioning member 82 and the receiving member 83 respectively. A movement of the driving shaft 86 in the rotation axis direction, is regulated by making a contact state between two C-rings (not shown) fitted to the driving shaft 86, and the positioning member 82 and the receiving member 83 respectively for example. The driving shaft 86 is a so-called round shaft having a circular shape in cross-section, and is supported rotatably in both directions of one direction and the other direction. The driving shaft 86 is disposed in parallel to the longitudinal direction of the base member 81. One end portion of the driving shaft 86 is disposed at substantially the same position as one end plate part 96 of the base member 81, and the other end portion is disposed at substantially the same position as the other end plate part 97 of the base member 81. Further, screw holes (not shown) are formed on both end portions of the driving shaft 86 respectively. Each screw hole is formed along the center axis direction of the driving shaft 86.

The first grooved member 87 is formed into a cylindrical shape. The first grooved member 87 is inserted into the hole part (not shown) provided on the first mover 84. A spiral groove 108 is formed on the outer peripheral surface of the first grooved member 87. The first grooved member 87 is coaxially fitted to the driving shaft 86 by a screw 111, in a state of engaging with one end portion of the driving shaft 86. The first grooved member 87 is rotated integrally with the driving shaft 86 in a state of fastening the screw 111, and is rotated separately (independently) from the driving shaft 86 in a state of loosening the screw 111.

The second grooved member 88 is formed into a cylindrical shape. The second grooved member 88 is inserted into the hole part provided on the second mover 85. A spiral groove 109 is formed on the outer peripheral surface of the second grooved member 88. In the spiral groove 109, a spiral direction is a reversed direction, compared with the spiral groove 108. Further, the pitch of the spiral groove 109 in the center axis direction of the second grooved member 88, is narrower than the pitch of the spiral groove 108 in the center axis direction of the first grooved member 87. The second grooved member 88 is coaxially fitted to the driving shaft 86 by a screw 112 in a state of engaging with the other end portion of the driving shaft 86. The second grooved member 88 is rotated integrally with the driving shaft 86 in a state of fastening the screw 112, and is rotated separately (independently) from the driving shaft 86 in a state of loosening the screw 112.

The driving force transmission mechanism 89 is a part for transmitting a driving force between the knob 90 and the driving shaft 86. More specifically, the driving force transmission mechanism 89 is a part for transmitting a rotation force to the driving shaft 86 when the knob 90 is rotated by a person who handles the attachment 80 (called an "operator" hereafter), thereby rotating the driving shaft 86.

Both of the two gears 91, 92 constituting the driving force transmission mechanism 89 are constituted using a bevel gear. Then, gears of the first gear 91 and gears of the second gear 92 are meshed with each other. Further, a rotary axis of the first gear 91 and a rotary axis of the second gear 92 are crossed each other vertically on the rotary axis of the driving shaft 86.

The first gear 91 is coaxially fitted to the driving shaft 86. The first gear 91 is fixed to the driving shaft 86 using a hexagon-holed set screw, etc., for example. Therefore, the driving shaft 86 and the first gear 91 are configured to be rotated integrally. Further, the first gear 91 is disposed between the positioning member 82 and the receiving member 83 in the rotation axis direction of the driving shaft 86.

The second gear 92 is coaxially fitted to an axis portion (not shown) which is formed integrally with the knob 90. The second gear 92 is fixed to the axis portion of the knob 90 using the hexagon-holed set screw, etc., for example. Therefore, the knob 90 and the second gear 92 are coaxially disposed and configured to be rotated integrally.

The knob 90 is rotary operated by the operator. The knob 90 is rotatably supported using an L-shaped plate 113. The L-shaped plate 113 is fixed to the bottom plate part 93 of the base member 81, for example by screwing or welding, etc.

An outermost peripheral surface of the knob 90 is knurled to suppress sliding, etc., during rotary operation.

Operation of the Attachment

Next, an operation of the attachment 80 having the above-mentioned structure will be described.

First, when the knob 90 is rotated by the operator in α1 direction, the second gear 92 is rotated integrally with the knob 90. When the second gear 92 is rotated, the rotation force is transmitted to the first gear 91. Therefore, when the second gear 92 is rotated, the first gear 91 is also rotated. Further, the first gear 91 is rotated in α2 direction integrally with the driving shaft 86.

As described above, when the driving shaft 86 is rotated, the first grooved member 87 and the second grooved member 88 are rotated in the α2 direction integrally with the driving shaft 86. In these rotations, when the first grooved member 87 is rotated, the operation is as follows. Namely, when the first grooved member 87 is rotated, the rotation force is transmitted to the first mover 84 by an engagement between the spiral groove 108 and the first engagement pin. Therefore, when the first grooved member 87 is rotated, the first mover 84 is moved in X1 direction. At this time, the first mover 84 moves in the rotation axis direction of the driving shaft 86 while being guided by the side plate parts 94, 95 of the base member 81. Further, the first mover 84 moves in a direction of approaching the end plate part 96 in the rotation axis direction of the driving shaft 86.

Meanwhile, when the second grooved member 88 is rotated, the operation is as follows. Namely, when the second grooved member 88 is rotated, the rotation force is transmitted to the second mover 85 by the engagement between the spiral groove 109 and the second engagement pin. Therefore, when the second grooved member 88 is rotated, the second mover 85 moves in the X2 direction. At this time, the second mover 85 moves in the rotation axis direction of the driving shaft 86 while being guided by the side plate parts 94, 95 of the base member 81. Further, the second mover 85 moves in a direction of approaching the end plate part 97 in the rotation axis direction of the driving shaft 86. Namely, when the knob 90 is rotated in the α1 direction, the first mover 84 and the second mover 85 are moved in a direction separating from each other in the rotation axis direction of the driving shaft 86.

Meanwhile, when the knob 90 is rotated by the operator in β1 direction, a rotating direction of the first gear 91, the second gear 92, and the driving shaft 86, and a rotating direction of the first grooved member 87 and the second grooved member 88 are opposite to the above rotating direction.

Namely, the first gear 91 is rotated in the β1 direction, and the second gear 92 and the driving shaft 86 are rotated in the β2 direction respectively. When the driving shaft 86 is rotated, the first grooved member 87 and the second grooved member 88 are rotated in the β2 direction integrally with the driving shaft 86. Therefore, a moving direction of the first mover 84 and the second mover 85 is also opposite to the above moving direction. Specifically, the first mover 84 moves in X3 direction which is a direction of approaching the receiving member 83, and the second mover 85 moves in X4 direction which is a direction of approaching the positioning member 82. Namely, when the knob 90 is rotated in the α2 direction, the first mover 84 and the second mover 85 are moved in a direction of approaching each other in the rotation axis direction of the driving shaft 86.

Further, in the above-mentioned series of operation, a rotational amount of the knob 90 and a moving amount of the first mover 84 are set in a proportional relation. Similarly, the rotational amount of the knob 90 and the moving amount of the second mover 85 are set in a proportional relation. However, the moving amount of the first mover 84 and the moving amount of the second mover 85 are different from each other, when the knob 90 is rotated by a specific amount. Specifically, the moving amount of the first mover 84 is larger than the moving amount of the second mover 85. This is because the groove pitch of the spiral groove 108 of the first grooved member 87 is set to be wider than the groove pitch of the spiral groove 109 of the second grooved member 88.

Further, regarding the first grooved member 87, as described above, by loosening the screw 111, only the first grooved member 87 can be rotated without rotating the driving shaft 86 (in a state that the driving shaft 86 is stopped). Actually, when the first grooved member 87 is rotated while the driving shaft 86 is stopped, the first mover 84 moves in accordance with the rotating direction and the rotation amount of the first grooved member 87. Accordingly, when the first mover 84 is moved by the rotary operation of the knob 90, an initial position for starting the movement of the first mover 84 (called a "first initial position" hereafter) can be arbitrarily adjusted by a single rotation of the first grooved member 87. Further, when a plurality of grooved members 87 with different groove pitch of the spiral groove 108 are prepared, the moving amount of the first mover 84 when performing a specific amount of rotation of the driving shaft 86 (namely, a relative ratio of the rotational amount of the driving shaft 86 and the moving amount of the first mover 84) can be adjusted (increased/decreased) by exchanging the first grooved member 87.

Similarly, regarding the second grooved member 88 as well, only second grooved member 88 can be rotated without rotating the driving shaft 86, by loosening the screw 112 as described above. Actually, when the second grooved member 88 is rotated while the driving shaft 86 is stopped, the second mover 85 moves in the center axis direction of the driving shaft 86 in accordance with the rotating direction and the rotational amount of the second grooved member 88. Accordingly, when the second mover 85 is moved by the rotary operation of the knob 90, the initial position for starting the movement of the second mover 85 (called a "second initial position" hereafter) can be arbitrarily adjusted by a single rotation of the second grooved member 88. Further, when a plurality of second grooved members 88 with different groove pitch of the spiral groove 109 are prepared, the moving amount of the second mover 85 when the driving shaft 86 is rotated by a specific amount, can be adjusted by exchanging the second grooved member 88.

Use Method of the Therapeutic Instrument Including the Attachment

Subsequently, explanation is given for a use method of the therapeutic instrument according to a third embodiment of the present invention.

When being roughly classified in time series, the use method of the therapeutic instrument according to the third embodiment is classified into a storing step and a pushing step, similarly to the first embodiment. In these steps, the pushing step is similar to a case of the first embodiment, and therefore only the storing step will be described in detail here.

Storing Step

The storing step is classified into a step performed before using the attachment 80 (called a "pre-step" hereafter), and a step performed using the attachment 80 (called a "post-step").

Pre-Step

First, the pre-step will be described. First, the inside of the syringe 68 of the syringe unit 22 is filled with the medical water, and thereafter the syringe unit 22 is mounted on the body unit 21. When the inside of the syringe 68 is filled with the medical water, prior to filling, the plunger 69 is set in a most pushed state, and from this state, the retraction of the plunger 69 is started. At this time, the plunger 69 is sufficiently retracted. Next, the advance movement of the nozzle member 23 is performed manually, and thereafter the plunger 69 of the syringe unit 22 is pushed, to thereby fill the inside of the tubular part 31 of the nozzle member 23 with the medical water. At this time, the plunger 69 is preferably pushed, with the body unit 21 inclined obliquely upward, so as not to allow bubbles to be remained in the tubular part 31.

Next, the supporting member 26 is protruded from the tip end of the tubular part 31 by causing the retreat movement of the nozzle member 23 manually. Thus, the supporting member 26 protruded from the tip end of the tubular part 31 is set in a state of being shaped into a form easy to be slightly curved in a developed shape. The above step is the pre-step. A work content performed in this pre-step is substantially the same as the work content performed in the first embodiment.

Post-Step

Next, the post-step will be described. First, as a precondition of the explanation, the attachment 80 is set in a previously specified initial state. The initial state of the attachment 80 is uniquely obtained by abutting of the first engagement pin (not shown) on the terminal end of the spiral groove 108 of the first mover 84, when the rotary operation of the knob 90 is performed so that the first mover 84 approaches the receiving member 83. In the initial state of the attachment 80, the first mover 84 is disposed at the first initial position, and the second mover 85 is disposed at the second initial position.

Figure 19:
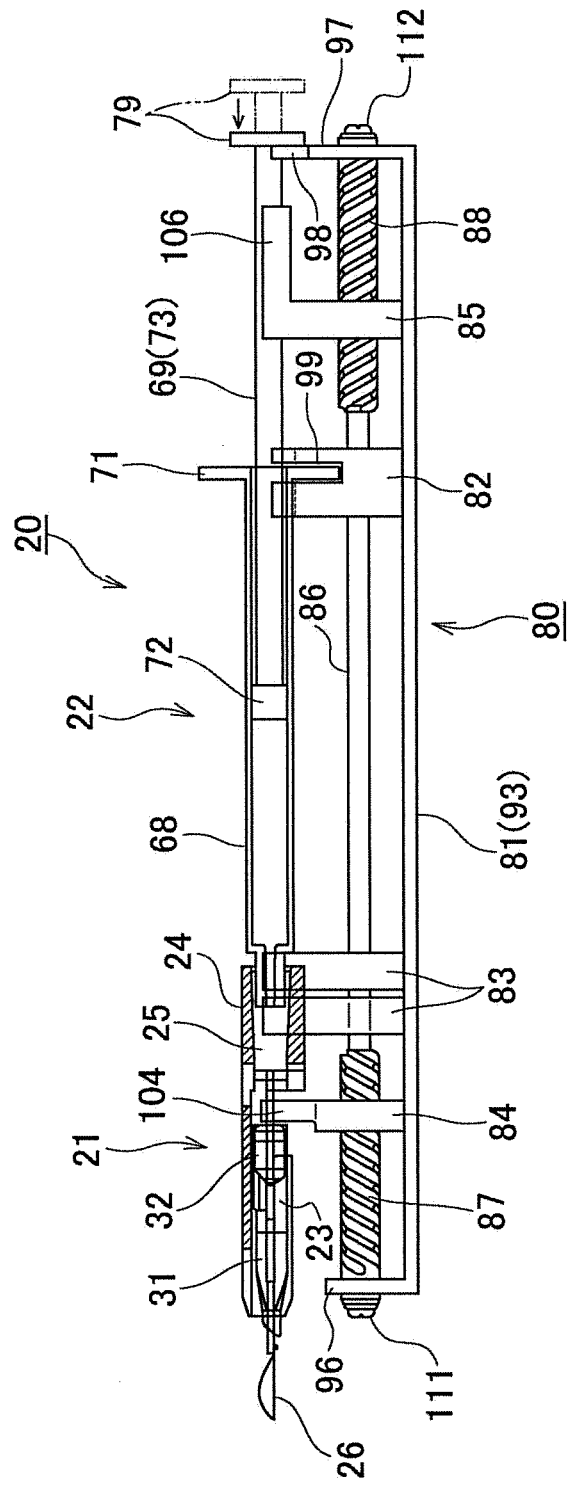
FIG. 19 is a view showing the use method of the therapeutic instrument according to the third embodiment of the present invention.

In the post-step, the therapeutic instrument 20 with the supporting member 26 curled, is set in the attachment 80 which is set in the initial state as described above (see FIG. 19). At this time, the therapeutic instrument 20 is set in the attachment 80 so that the supporting member 26 previously formed to be easy to be curled, is curved into a protruded shape downward. Further, the holding member 24 of the body unit 21 is fitted into the unit receiving part 103 of the receiving member 83, and the flange part 71 of the syringe unit 22 is inserted into the slit part 99 of the positioning member 82. Then, the relative position of the attachment 80 and the therapeutic instrument 20 is determined in the rotation axis direction of the driving shaft 86.

Further, a flange 79 formed on the rear end portion of the rod part 73 of the plunger 69 is adjusted to be positioned more outside than the end plate part 97 of the base member 81, before the therapeutic instrument 20 is set in the attachment 80. Specifically, in the pre-step, the retraction amount and the pushing amount of the plunger 69 are adjusted in the pre-step. Then, after the therapeutic instrument 20 is set in the attachment 80, the plunger 69 is slowly pushed, so that the flange 79 abuts on the end plate part 97. Thus, the position of the rod part 73 is uniquely determined in the rotation axis direction of the driving shaft 86. In this case as well, the plunger 69 is preferably pushed, with the body unit 21 inclined obliquely upward together with the attachment 80, so as not to allow the bubbles to be remained in the tubular part 31. Further, a pedestal (not shown) for supporting the attachment 80 from below to obtain the above-mentioned inclination, may be fitted to a lower surface of the bottom plate part 93 of the base member 81 by screws, etc.

Actually, when the plunger 69 is pushed, a part of the medical water with which the inside of the syringe 68 is filled, is discharged toward the supporting member 26 from the tip end of the nozzle member 23. The supporting member 26 has a curved surface curved into a protruded shape downward, and therefore the medical water discharged from the tip end of the nozzle member 23, is accumulated on the curved surface of the supporting member 26.

Next, the previously prepared corneal endothelium layer is placed on the supporting member 26 using an instrument such as tweezers, etc., for example. At this time, a part of the medical water discharged before is accumulated on the curved surface of the supporting member 26, and therefore the corneal endothelium layer is placed thereon. Next, the corneal endothelium layer on the supporting member 26 is coated with a suitable amount of liquid made of the viscoelastic substance (or the liquid is delivered thereto). A work of placing the corneal endothelium layer on the supporting member 26, and a work of delivering the liquid to the corneal endothelium layer, may be performed similarly to the first embodiment.

Next, the knob 90 of the attachment 80 is rotated. Then, the first mover 84 and the second mover 85 are moved in the direction of separating from each other, according to the rotation of the knob 90. When the rotation of the knob 90 is continued, the presser 104 of the first mover 84 abuts on the finger rest part 32 of the nozzle member 23. Thereafter, the nozzle member 23 performs the advance movement according to the movement of the first mover 84 which is associated in conjunction with the rotation of the knob 90. Therefore, the timing of the start of the relative movement of the nozzle member 23 with respect to the needle member 25, is the timing when the presser 104 of the first mover 84 abuts on the finger rest part 32 of the nozzle member 23.

Meanwhile, the presser 106 of the second mover 85 abuts on the flange 79 of the rod part 73, after the presser 104 of the first mover 84 abuts on the finger rest part 32 of the nozzle member 23 as described above. Thereafter, the rod part 73 is drawn out according to the movement of the second mover 85 which is associated in conjunction with the rotation of the knob 90. Therefore, the timing when the rod part 73 starts to move, is the timing when the presser 106 of the second mover 85 abuts on the flange 79 of the rod part 73. A positional interference between the second mover 85 and the end plate part 97 is avoided by disposing two pressers 106 so as to stride across the protrusion 98 formed on the end plate part 97.

At this time, the rotational amount of the knob 90 required for abutting of the presser 106 of the second mover 85 on the flange 79 of the rod part 73, after abutting of the presser 104 of the first mover 84 on the finger rest part 32 of the nozzle member 23, corresponds to a "required driving amount" in the present invention. However, the "required driving amount" includes not only the required rotational amount of the knob 90, but also an operation amount of other member operated in conjunction with the rotation of the knob 90 (for example, the rotational amount of the driving shaft 86, the moving amount of the first mover 84, and the moving amount of the second mover 85, etc.).

The required rotational amount of the knob 90 is set as follows.

First, when the nozzle member 23 performs the advance movement by being pushed by the first mover 84, similarly to a case of the first embodiment, the corneal endothelium layer on the supporting member 26 begins to enter into the space 33 in the tubular part 31 together with the supporting member 26. At this time, the supporting member 26 is brought into contact with the opening 34 of the tubular part 31 in the middle of advancement of the nozzle member 23, to thereby gradually deform the supporting member 26 into the U-shape, and deform the corneal endothelium layer in the same way.

Therefore, the required rotational amount of the knob 90 is set to satisfy any one of the following conditions (1) to (3).

(1) The presser 106 of the second mover 85 abuts on the flange 79 of the rod part 73, before the supporting member 26 begins to be deformed by the advance movement of the nozzle member 23.

(2) The presser 106 of the second mover 85 abuts on the flange 79 of the rod part 73 before the corneal endothelium layer on the supporting member 26 begins to enter into the space 33 in the tubular part 31, after the supporting member 26 is deformed by the advance movement of the nozzle member 23.

(3) The presser 106 of the second mover 85 abuts on the flange 79 of the rod part 73, after the corneal endothelium layer on the supporting member 26 begins to enter into the space 33 in the tubular part 31 by the advance movement of the nozzle member 23.

As described above, when the presser 106 of the second mover 85 abuts on the flange 79 of the rod part 73, thereafter, the plunger 69 is drawn out according to the movement of the second mover 85 associated in conjunction with the rotation of the knob 90. Further, when the knob 90 is rotated, the first mover 84 and the second mover 85 are concurrently moved accordingly. Namely, when the first mover 84 moves in the X1 direction, the second mover 85 is concurrently moved in the X2 direction. Therefore, the advance movement of the nozzle member 23 by the first mover 84, and the drawing movement of the plunger 69 by the second mover 85 are concurrently performed. Accordingly, the negative pressure can be caused to act in the space 33 of the tubular part 31, by the drawing movement of the plunger 69, while retracting the corneal endothelium layer on the supporting member 26 into the space 33 of the tubular part 31.

Thereafter, the knob 90 is further rotated, to thereby make the nozzle member 23 more advanced, until the blade part 37 of the nozzle member 23 (see FIG. 4) abuts on the tip end portion of the slit 50 (see FIG. 7) of the holding member 24. Thus, the corneal endothelium layer on the supporting member 26 is set in a completely stored state in the tubular part 31. Further, the tip end side of the tubular part 31 is set in a closed state by the liquid which is sucked together with the corneal endothelium layer. Thereafter, the therapeutic instrument 20 is removed from the attachment 80. As described above, the storing step is completed.

9. Effect of the Third Embodiment

According to the third embodiment of the present invention, the following effect can be obtained, in addition to the effect similar to the effect of the first embodiment.

Namely, in the storing step of the first embodiment, an operation for the advance movement of the nozzle member 23, and an operation for the retraction movement of the plunger 69 are performed manually. Therefore, when the corneal endothelium layer is retracted into the tubular part 31 of the nozzle member 23 and stored therein together with the supporting member 26, a work of advancing the nozzle member 23 and a work of retracting the plunger 69 need to be respectively performed carefully. Further, even if each work is performed carefully, variation is generated in a position for advancing the nozzle member 23, and a position for retracting the plunger 69 even by the same person, and individual variation is also generated.

Meanwhile, in the storing step of the third embodiment, the operation for performing the advance movement of the nozzle member 23, and the operation for performing the drawing movement of the plunger 69 are performed by the attachment 80. Therefore, a speed for performing the advance movement of the nozzle member 23, and a speed for performing the drawing movement of the plunger 69 can be easily and suitably adjusted by the rotary operation of the knob 90. Further, the position for advancing the nozzle member 23, and the position for drawing the plunger 69 are mechanically determined by the attachment 80, and therefore neither variation nor individual variation is generated. Accordingly, by setting the relative positional relation of the movers 84, 85 in the rotation axis direction of the driving shaft 86 in an optimal state for example which is previously obtained by an experiment, the corneal endothelium layer can be suitably and surely stored in the space 33 in the tubular part 31, without being influenced by a skill, etc., of an operator.

Further, by using the attachment 80, the retraction movement of the corneal endothelium layer on the supporting member 26 into the space 33 in the tubular part 31, and an operation of causing the negative pressure in the space 33 in the tubular part 31, can be concurrently and inter-connectedly performed. Therefore, the corneal endothelium layer can be more surely stored in the tubular part 31, even by a person having no skill and not familiar with handling of the therapeutic instrument 20 and the attachment 80. Particularly, the corneal endothelium layer prepared for the corneal endothelium layer transplant surgery, is collected from a donor, and cultured. Therefore, when the corneal endothelium layer is stored in the tubular part 31, an error due to an inappropriate power adjustment is not permitted. Accordingly, in order to prevent an occurrence of such a human error, it is extremely preferable to use the attachment 80 in the storing step.

Regarding the required rotational amount of the knob 90, the knob 90 can be arbitrarily adjusted, by carrying out a single rotation of the first grooved member 87 corresponding to the first mover 84, or carrying out a single rotation of the second grooved member 88 corresponding to the second mover 85, or carrying out a single rotation of both members. Therefore, the negative pressure can be caused to act at a desired timing in a process of retracting the corneal endothelium layer on the supporting member 26 into the tubular part 31 of the nozzle member 23. Also, the timing of abutting the presser 106 of the second mover 85 on the flange 79 of the plunger 69 can be adjusted beforehand, depending on the shape and the state of the corneal endothelium layer. Therefore, further detailed adjustment can be performed, in accordance with the shape or the state, etc., of the corneal endothelium layer used for the corneal endothelium layer transplant surgery.

Further, by exchanging at least one of the grooved members of the first grooved member 87 and the second grooved member 88, with another grooved member having a different pitch, a ratio of the relative moving amount of the first mover 84 with respect to the second mover 85, can be changed. Therefore, further detailed adjustment can be performed, in accordance with the shape or the state, etc., of the corneal endothelium layer used for the corneal endothelium layer transplant surgery.

In this specification, regarding the operation of the plunger 69 for causing the negative pressure to act, an operation performed manually directly without using the attachment 80 is described as the "retracting operation", and an operation performed using the attachment 80 is described as the "drawing operation". There is no change in both operations, in the point of moving the plunger 69 relatively to the syringe 68 in one direction.

10. Fourth Embodiment

Structure of the Therapeutic Instrument

Figure 20:
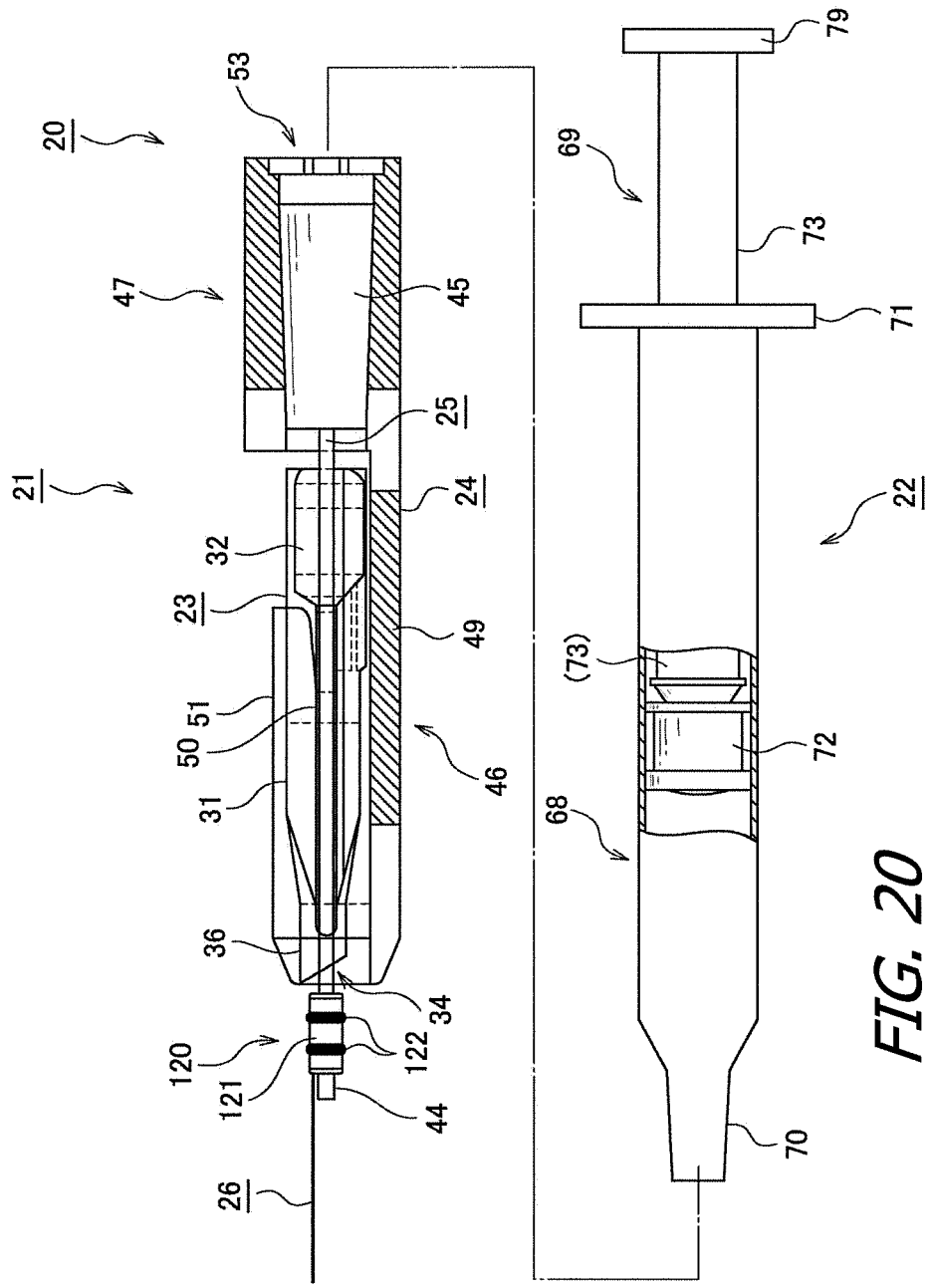
FIG. 20 is a side, partial cross-sectional view of the therapeutic instrument according to a fourth embodiment of the present invention.

FIG. 20 is a cross-sectional view describing the structure of the therapeutic instrument according to a fourth embodiment of the present invention. The therapeutic instrument 20 of the fourth embodiment is different from that of the first embodiment, particularly in the following point. Namely, in the first embodiment, the valve member 27 (see FIG. 3) is mounted on the nozzle member 23. However, the fourth embodiment employs a structure of using a movable stopper 120, without using the valve member 27. In the description hereafter, the same signs and numerals are assigned to constitutional elements similar to those of the first embodiment, and an overlapped description is omitted as much as possible, and the structure, etc., of the therapeutic instrument of the fourth embodiment is described focusing on a point different from the first embodiment.

Structure of the Movable Stopper

The movable stopper 120 corresponds to the "attached unit" for causing the negative pressure to act in the tubular part 31 by the relative movement of the nozzle member 23 and the needle member 25. The movable stopper 120 is mainly constituted of a stopper body 121, and two seal members 122. In these elements, the above-mentioned supporting member 26 is integrally formed on the stopper body 121.

Stopper Body

Figure 21A:
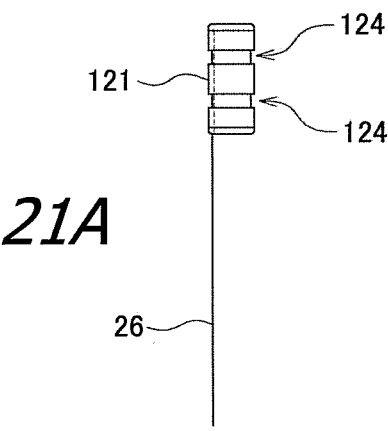
FIGS. 21A-21C are side, end and plan views of a stopper body.
Figure 21B:
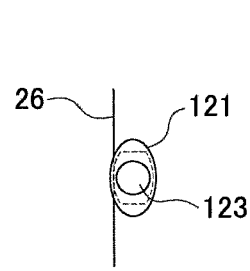
Figure 21C:
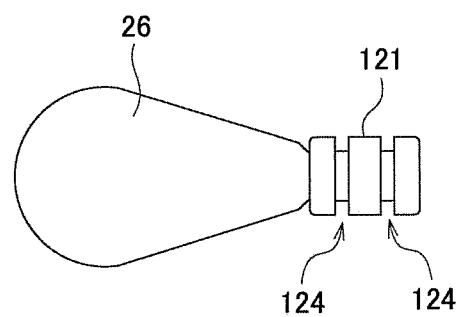

FIG. 21 is a trihedral view showing the structure of the stopper body. The stopper body 121 is obtained by integral molding of resin, for example. The stopper body 121 has a cylindrical structure as a whole, and a through hole 123 is formed on its center axis. A hole diameter of the through hole 123 corresponds to the outer diameter of needle part 44. The stopper body 121 is an oval outer shape viewed from the center axis direction. The shape and the dimension of the oval shape correspond to the sectional shape and the hole diameter of the space 33 (see FIG. 4) in the tubular part 31, and correspond to the shape and the dimension of the openings 34, 35 communicated with the space 33.

Two (double) grooves 124 are formed on the outer peripheral part of the stopper body 121. The two grooves 124 are formed, with their positions deviated in the center axis direction of the stopper body 121. Further, each groove 124 is formed into a recessed shape in cross-section over the whole periphery of the stopper body 121. The supporting member 26 extends from one end portion of the stopper body 121, in the center axis direction of the stopper body 121. The supporting member 26 is disposed approximately in parallel to the center axis of the stopper body 121. The supporting member 26 has a planar eggplant shape as a whole.

Seal Member

Figures 22A, 22B:
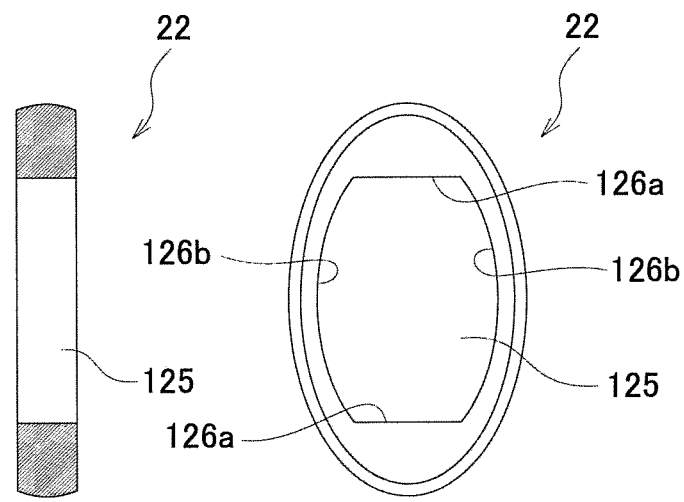
FIGS. 22A-22B are section and plan views of a seal member.

FIG. 22 is a dihedral view showing the structure of the seal member. The seal member 122 is formed using synthetic rubber such as silicone rubber or fluororubber. The seal member 122 is a ring-like member having a hole 125. The outer shape of the seal member 122 is an oval shape similarly to the outer shape of the above-mentioned stopper body 121. The shape of the hole 125 corresponds to the outer peripheral shape of a part where the groove 124 of the stopper body 121 is formed. Specifically, the shape of the hole 125 is formed into a barrel shape as a whole, by two straight line-shaped side parts 126a facing each other in a long axis direction of the seal member 122, and two arc-shaped side parts 126b facing each other in a short axis direction of the seal member 122.

Figure 23A:
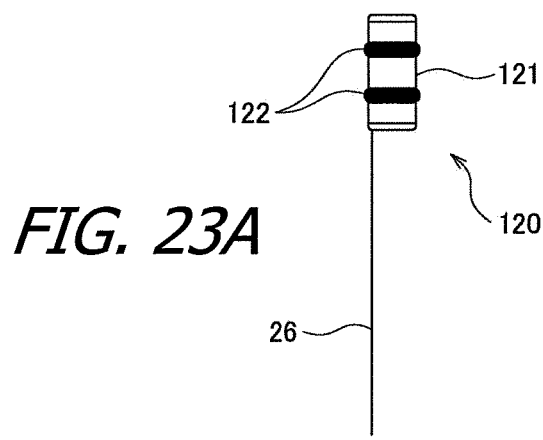
FIGS. 23A-23C are side, end and plan views of a movable stopper.
Figure 23B:
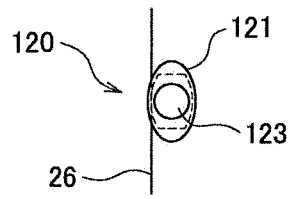
Figure 23C:
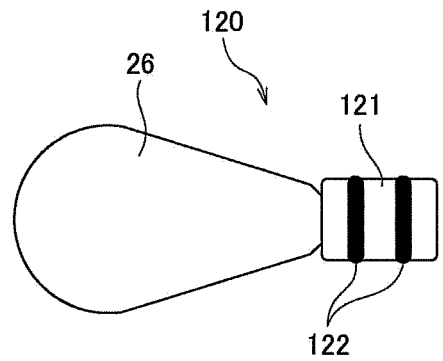

FIG. 23 is a trihedral view showing the structure of the movable stopper. The movable stopper 120 shown in the figure is obtained by fitting seal members 122 into two grooves 124 of the stopper body 121 so as to engage with the grooves 124. In this case, an outermost peripheral part of the two seal members 122 are disposed in a state of slightly swelling outward from the outermost peripheral part of the stopper body 121.

Figure 24:
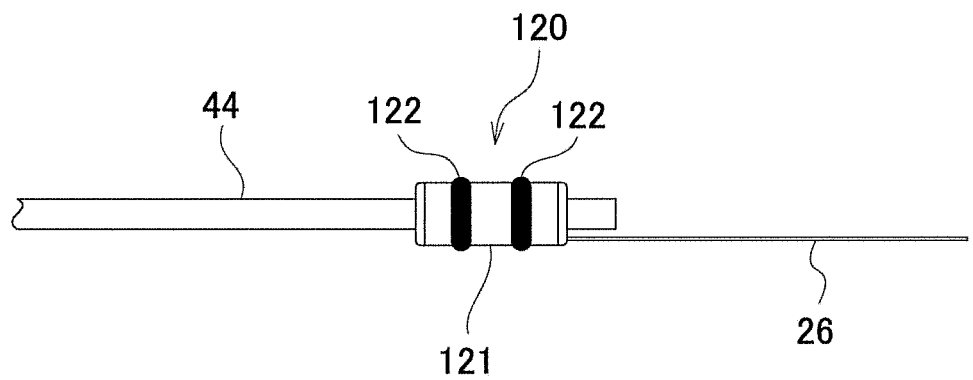
FIG. 24 is a view showing a state that the movable stopper is attached to a needle part.

FIG. 24 is a view showing a state that the movable stopper is attached to the needle part. When the movable stopper 120 is attached to the needle part 44, the stopper body 121 is inserted into the needle part 44 from the tip end side of the needle part 44. Specifically, the through hole 123 of the stopper body 121 is engaged with the needle part 44. At this time, a specific portion of the tip end of the needle part 44 is set in a state of protruding from the end portion of the stopper body 121, so that the tip end of the needle part 44 is disposed to face the position where the corneal endothelium layer 2e (see FIG. 12) is supported on the supporting member 26. Further, the stopper body 121 is fixed to the needle part 44, for example using an adhesive agent suitable for medical use, so that the stopper body 121 is not moved in the center axis direction of the needle part 44. Thus, the movable stopper 120 is engaged with the needle part 44 and fixed thereto.

Movement

Figure 25:
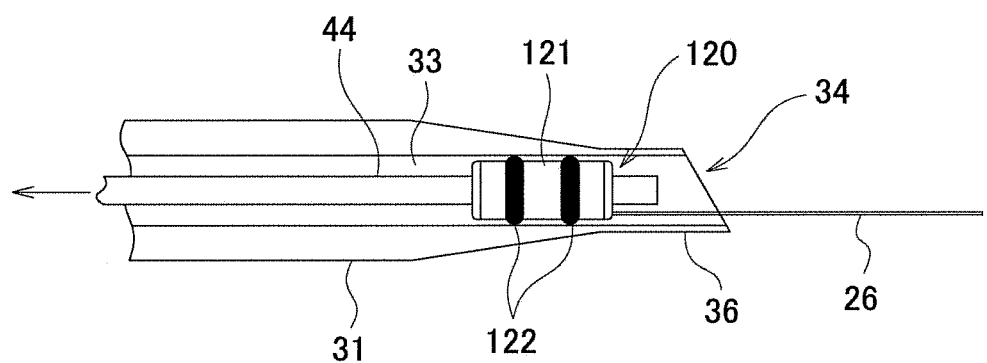
FIG. 25 is a view showing a state that the nozzle member and the needle part are relatively moved so as to draw the supporting member into a tubular part.

When the nozzle member 23 and the needle part 44 are relatively moved so as to retract the supporting member 26 into the tubular part 31 in the therapeutic instrument 20 including the movable stopper 120 having the above-mentioned structure, the movable stopper 120 (the stopper body 121 and the seal members 122) is disposed in the tubular part 31 as shown in FIG. 25. In this tubular part 31, the movable stopper 120 moves in the tubular part 31 integrally with the needle part 44 while sealing the space 33 in the tubular part 31. An air-tightly sealed state by the movable stopper 120 is maintained by movement (sliding) of the two seal members 122 mounted on the stopper body 121, in contact with the inner peripheral surface of the space 33. Therefore, for example if the nozzle member 23 and the needle part 44 are relatively moved so as to retract the supporting member 26 into the tubular part 31 in a state of closing the hole of the base part 45 of the needle part 25 by a finger, etc., the negative pressure is generated in the tubular part 31 of the nozzle member 23, which is associated in conjunction with the movement of the movable stopper 120.

A body portion (the stopper body 121) of the movable stopper 120 excluding the supporting member 26 may be disposed as follows. Namely, when the nozzle member 23 and the needle part 44 are relatively moved so as to retract the supporting member 26 into the tubular part 31, the body portion of the movable stopper 120 is disposed in the tubular part 31 before starting the movement, or it is disposed in the tubular part 31 after starting the movement.

Use Method

Next, a use method of the therapeutic instrument according to a fourth embodiment of the present invention will be described. Note that in this description, the same content as the content of the use method described in the first embodiment is simply described, and a different content will be described in detail.

Storing Step

First, as the state of the body unit 21, the nozzle member 23 is set in a most retreated state. Then, the supporting member 26 is set in a most protruded state from the tip end of the nozzle member 23. At this time, the supporting member 26 is set in a planarly developed state. In this state, the inside of the syringe 68 of the syringe unit 22 is filled with the medical water in advance. Subsequently, the syringe unit 22 is mounted on the body unit 21. Specifically, the insertion part 70 of the syringe 68 is inserted into the base part 45 of the needle member 25 and connected thereto. Thus, when the tip end of the syringe 68 is connected to the base part 45 of the needle member 25, the base part 45 of the needle member 25 is substantially set in a closed state by the syringe unit 22. This is because the sliding part 72 of the plunger 69 is inserted into the syringe 68, and the movement of fluid (liquid or gas) passing through the needle part 44 is regulated by a sealing function of the sliding part 72.

Next, similarly to the first embodiment, after the advance movement of the nozzle member 23, the inside of the tubular part 31 of the nozzle member 23 is filled with the medical water. Subsequently, the inside of the tubular part 31 of the nozzle member 23 is filled with the medical water by pushing a specific portion of the plunger 69 of the syringe unit 22, and thereafter the nozzle member 23 is retreated. Next, after the therapeutic instrument 20 is vertically inverted, the previously prepared corneal endothelium layer 2e (see FIG. 11(D)) is placed on the supporting member 26. Next, the liquid 75 is delivered to the corneal endothelium layer 2e.

Next, the nozzle member 23 is slowly advanced so as not to add an excessive load on the corneal endothelium layer 2e on the supporting member 26. Then, the corneal endothelium layer 2e supported by the supporting member 26 begins to enter into the space 33 in the tubular part 31 together with the supporting member 26. At this time, the movable stopper 120 is disposed in the tubular part 31 prior to the corneal endothelium layer 2e. Further, the movable stopper 120 moves through the tubular part 31, associated in conjunction with the advance movement of the nozzle member 23. Then, air flows into the space 33 in the tubular part 31 from the opening 34 of the beak part 36. Therefore, the negative pressure is generated in the space 33 in the tubular part 31, in an area closer to the opening 34 than the movable stopper 120.

Further, as described above, when the liquid (preferably the viscoelastic substance) 75 is delivered to the corneal endothelium layer 2e, the opening 34 of the beak part 36 is closed by the liquid 75 when the supporting member 26 is retracted into the tubular part 31. Then, the space 33 disposed at more tip end side than the movable stopper 120 is set in an air-tightly sealed state in combination with the sealing function of the movable stopper 120. The movable stopper 120 moves through the tubular part 31 while maintaining such an air-tightly sealed state. Then, the corneal endothelium layer 2e is gradually retracted into the tubular part 31 together with the supporting member 26, associated in conjunction with the movement of the movable stopper 120. When the nozzle member 23 is set in the most advanced state, the corneal endothelium layer 2e is set in a state of being completely stored in the space 33 in the tubular part 31.

Pushing Step

In the pushing step, the plunger 69 is pushed in a state that the tip end of the nozzle member 23 of the therapeutic instrument 20 that ends the storage of the corneal endothelium layer 2e by the above-mentioned storing step is inserted into the corneal portion of the eyeball 1 (see FIG. 14(A) to FIG. 14(C)). Then, the positive pressure acts in the space 33 in the tubular part 31 by push of the plunger 69. By receiving the positive pressure, the corneal endothelium layer 2e in the tubular part 31, is pushed out to the outside of the tubular part 31 together with the liquid 75. Thus, the corneal endothelium layer 2e is inserted (delivered) into the anterior chamber 5 (see FIG. 1).

11. Effect of the Fourth Embodiment

According to the therapeutic instrument of the fourth embodiment, the following specific effect can be obtained, particularly compared with the first embodiment.

Namely, when the corneal endothelium layer 2e is stored in the tubular part 31 of the nozzle member 23, the negative pressure is caused to act in the space 33 in the tubular part 31 only by relatively moving the nozzle member 23 and the holding member 24, and by utilizing this negative pressure, the corneal endothelium layer 2e can be smoothly stored in the tubular part 31, even when the retracting operation of the syringe unit 22 is not performed like the first embodiment. Further, when the liquid 75 is previously delivered to the corneal endothelium layer 2e, the corneal endothelium layer 2e can be naturally retracted into the tubular part 31, by air-tightly sealing the space 33 at the tip end side in the tubular part 31 by the liquid 75 and the movable stopper 120, and moving the movable stopper 120 while maintaining the sealed state.

12. Modified Example, Etc.

A technical range of the present invention is not limited to the above-mentioned embodiment, and includes a variously modified or improved embodiment in a range capable of deriving a specific effect obtained by the constituting features of the invention and by combining these constituting features.

For example, in the above-mentioned each embodiment, a pressure generator is constituted using the syringe unit 22. However, the present invention is not limited thereto, and for example the pressure generator may be constituted by combining a tube and a pump, etc. However, use of the syringe unit 22 is preferable, in terms of a cost, operability, and maintenance, etc.

Further, as a modified example of the second embodiment, a structure in combination with the needle member 25 can also be employed. Specifically, the base part 45 of the needle member 25 is engaged with the rear end of the nozzle member 23 and fixed thereto, in a state that the tip end of the needle part 44 is disposed facing the inside of the tubular part 31. Then, the syringe unit 22 is connected to the base part 45 of the needle member 25. In this case, a length of the needle part 44 is set to be sufficiently short, so that the tip end of the needle part 44 does not touch on the corneal endothelium layer 2e stored in the tubular part 31.

Further, in the third embodiment, regarding the attachment 80, when the corneal endothelium layer is stored in the tubular part 31 of the therapeutic instrument 20, the therapeutic instrument 20 and the attachment 80 are combined into one, and when the corneal endothelium layer is delivered to an affected part, the therapeutic instrument 20 and the attachment 80 are separated from each other. However, the present invention is not limited thereto. For example, although not shown, a mechanism having a function similar to the function of the attachment 80 can also be integrally provided to the therapeutic instrument 20.

Further, in the third embodiment, the rotary operation of the knob 90 is performed manually. However, the present invention is not limited thereto, and the rotary operation of the knob 90 may be performed automatically using a motor, etc. Further, a portion of the L-shaped plate 113 may be formed integrally with the base member 81.

Further, as a structure of uniquely reproducing the initial state of the attachment 80, the first engagement pin (not shown) is abutted on the terminal end of the spiral groove 108 of the first mover 84. However, the present invention is not limited thereto, and for example the following structure may be employed. Namely, when the knob 90 is rotated so that the first mover 84 approaches the receiving member 83, the initial state of the attachment 80 is uniquely reproduced, by making the first mover 84 or the second mover 85 abut on a stopper part (not shown) provided on the base member 81 in advance.

Further, the attached unit may have the following structure as the structure of causing the negative pressure to act in the tubular part by the relative movement of the nozzle member and the needle member: for example, when the negative pressure is caused by the pressure generator using the pump, etc., the negative pressure is caused by operating the pump by switching, in conjunction with the relative movement of the nozzle member 23 and the needle member 25.

Further, the fourth embodiment employs the structure of forming the supporting member 26 integrally with the movable stopper 120 as a preferable example. However, the present invention is not limited thereto, and a structure of fitting the supporting member 26 to the needle part 44 as a member separated from the movable stopper 120, may also be employed.

Further, in order to satisfy both the facility in moving the movable stopper 120 and a satisfactory sealability in a well-balanced state, the fourth embodiment employs the structure of providing two seal members 122, with positions deviated from each other in the center axis direction of the stopper body 121. However, the present invention is not limited thereto, and a structure of providing one seal member 122, or a structure of providing three or more seal members 122, may also be employed.

DESCRIPTION OF SIGNS AND NUMERALS

1 Eyeball
2 Cornea
2e Corneal endothelium layer
20 Therapeutic instrument
21 Body unit
22 Syringe unit
23 Nozzle member
24 Holding member
25 Needle member
26 Supporting member
27 Valve member
28 Connection piece
32 Finger rest part
33 Space
34 Opening
41 Through hole
44 Needle part
46 First holding part
47 Second holding part
75 Liquid
80 Attachment
84 First mover 85 Second mover
86 Driving shaft
87 First grooved member
88 Second grooved member
89 Driving power transmission part
90 Knob
120 Movable stopper

The invention claimed is:

1. A therapeutic instrument for storing and delivering a sheet-type therapeutic substance, the therapeutic instrument comprising:
   a nozzle member having a tubular part defining an inner surface, a storage space that is configured to store the therapeutic substance in a deformed state, a tip end with an opening extending therethrough for charging and discharging the therapeutic substance, and a rear communication part for communicating with the storage space;
   a flexible support member that is configured to support the sheet-type therapeutic substance and is movable relative to the nozzle member between a retracted position where a portion of the inner surface of the tubular part deforms the flexible support member and an extended position where the flexible support member is located outside the tubular part;
   a stopper, which is movable relative to the nozzle member, that engages the portion of the inner surface of the tubular part that deforms the flexible support member to create an air-tight seal between the stopper and the nozzle member at a location adjacent to the tip end;
   a needle member, which is movable with the stopper, having a hollow needle part with an open tip end that is located outside of the flexible support member; and
   a pressure generator that selectively generates a negative pressure and a positive pressure within the tubular part of the nozzle member between the stopper and the tip end,
   wherein the negative pressure draws the therapeutic substance into the tubular part, and
   wherein the positive pressure pushes the therapeutic substance out of the tubular part when the therapeutic substance stored in the tubular part.

2. The therapeutic instrument according to claim 1, wherein the needle member is secured to the flexible support member and the hollow needle part inserted into the tubular part of the nozzle member through the rear communication part.

3. The therapeutic instrument according to claim 2, wherein the support member comprises a tongue-like member having a planar developed shape in a state that the tip end of the needle part is protruded to outside of the tubular part, and having a shape deformed into a roll-shape in contact with an edge of the opening of the tubular part when the tip end of the needle part is retracted into the tubular part through the opening.

4. The therapeutic instrument according to claim 2, wherein the rear communication part is a hole provided on the rear end of the tubular part, and the needle part is engaged with the hole.

5. The therapeutic instrument according to claim 2, wherein the stopper is engaged with the needle part and fixed thereto and moves through the tubular part together with the needle part while air-tightly sealing the storage space in the tubular part.

6. The therapeutic instrument according to claim 2, further comprising
   a holding member having a first holding part that holds the nozzle member in a state that the nozzle member and the needle member are allowed to move relatively to each other, and a second holding part that holds a base part of the needle member in a fixed state.

7. The therapeutic instrument according to claim 6, wherein the holding member has a unit for regulating a movement terminal end position when the nozzle member and the needle member are relatively moved.

8. The therapeutic instrument according to claim 2, comprising an attached unit for causing the negative pressure to act in the tubular part by a relative movement of the nozzle member and the needle member.

9. The therapeutic instrument according to claim 8, wherein the pressure generator has a movable part that selectively causes the negative pressure and the positive pressure to act in the tubular part of the nozzle member through the hole, and the attached unit includes a first moving unit that relatively moves the nozzle member and the needle member; a second moving unit that moves the movable part of the pressure generator; and a driving unit that concurrently moves the first moving unit and the second moving unit.

10. The therapeutic instrument according to claim 9, wherein the driving unit moves the first moving unit and the second moving unit, so that the second moving unit starts to move the movable part of the pressure generator, after the first moving unit starts to move the nozzle member and the needle member relatively.

11. The therapeutic instrument according to claim 8, wherein the attached unit is composed of the stopper engaged with the needle part and fixed thereto, and the stopper causes the negative pressure to be generated in the tubular part by integral movement of the nozzle member and the needle part in the tubular part while air-tightly sealing the storage space in the tubular part, when the nozzle member and the needle member are relatively moved so as to retract the support member into the tubular part.

12. The therapeutic instrument according to claim 11, wherein the support member is formed integrally with the stopper.

13. The therapeutic instrument according to claim 1, wherein the negative pressure draws the therapeutic substance and a liquid on the therapeutic substance into the tubular part, and the positive pressure pushes the therapeutic substance and liquid out of the tubular part.

14. The therapeutic instrument according to claim 1, wherein the pressure generator comprises a syringe unit having a syringe and a plunger.

* * * * *